(12) United States Patent
Iyengar et al.

(10) Patent No.: US 9,244,000 B2
(45) Date of Patent: Jan. 26, 2016

(54) ANALYTE TEST STRIP AND ANALYTE METER DEVICE

(75) Inventors: Sridhar Iyengar, Salem, NH (US); Ian Harding, Wells (GB); Charles Boiteau, Carlisle, MA (US); Collin Butters, Pelham, NH (US)

(73) Assignee: AgaMatrix, Inc., Salem, NH (US)

(*) Notice: Subject to any disclaimer, the term of this patent is extended or adjusted under 35 U.S.C. 154(b) by 207 days.

(21) Appl. No.: 13/808,736

(22) PCT Filed: Jun. 30, 2011

(86) PCT No.: PCT/US2011/042572
§ 371 (c)(1),
(2), (4) Date: Feb. 21, 2013

(87) PCT Pub. No.: WO2012/006210
PCT Pub. Date: Jan. 12, 2012

(65) Prior Publication Data
US 2013/0146478 A1   Jun. 13, 2013

Related U.S. Application Data

(60) Provisional application No. 61/362,229, filed on Jul. 7, 2010.

(51) Int. Cl.
*G01N 27/327* (2006.01)
*G01N 21/25* (2006.01)
(Continued)

(52) U.S. Cl.
CPC .......... *G01N 21/255* (2013.01); *G01N 21/7703* (2013.01); *G01N 21/8483* (2013.01); *G01N 33/48771* (2013.01)

(58) Field of Classification Search
CPC .......... G01N 21/255; G01N 27/327–27/3274; G01N 21/8483; G01N 21/7703; G01N 33/48771; G02B 6/0011–6/0095

USPC ......... 204/403.01–403.15; 205/775, 789, 792
See application file for complete search history.

(56) References Cited

U.S. PATENT DOCUMENTS

| 3,907,503 A | 9/1975 | Betts et al. |
| 4,711,245 A | 12/1987 | Higgins et al. |

(Continued)

FOREIGN PATENT DOCUMENTS

| JP | H11-235196 A | 8/1999 |
| WO | 2009032657 A1 | 3/2009 |

OTHER PUBLICATIONS

Raine, C. H. III et al, Significant Insulin Dose Errors May Occur if Blood Glucose Results Are Obtained from Miscoded Meters, Journal of Diabetes Science and Technology, Mar. 2007, p. 205-210, vol. 1, Issue 2.

*Primary Examiner* — J. Christopher Ball
(74) *Attorney, Agent, or Firm* — Larson & Anderson, LLC

(57) ABSTRACT

A test strip with an incorporated optical waveguide and deflectors punched through the optical waveguide allows light to exit through a layer of the test strip and be detected by a photo detector. Using light and a photodetector, these uniquely coded strips are identified. The waveguide can be constructed by sandwiching two layers of the test strip around a light transmissible layer. This configuration allows light to be transmitted through the test strip and out the other end, as well as allowing some light to escape the deflector. This light is detected by a photodetector mounted in the analyte test meter. The deflectors may be placed in patterns such that detection of this light indicates certain characteristics of the strip, such as non-counterfeit, regional identification, type of analyte tested, and coding information.

47 Claims, 24 Drawing Sheets

(51) Int. Cl.
    *G01N 21/77* (2006.01)
    *G01N 21/84* (2006.01)
    *G01N 33/487* (2006.01)

(56) References Cited

U.S. PATENT DOCUMENTS

| | | | |
|---|---|---|---|
| 5,352,351 A | 10/1994 | White et al. | |
| 5,437,999 A | 8/1995 | Diebold et al. | |
| 5,565,085 A | 10/1996 | Ikeda et al. | |
| 5,628,890 A | 5/1997 | Carter et al. | |
| 7,344,626 B2 | 3/2008 | Harding et al. | |
| 2003/0049168 A1 | 3/2003 | Patel et al. | |
| 2003/0138356 A1 | 7/2003 | Gilmour et al. | |
| 2005/0258035 A1 | 11/2005 | Harding et al. | |
| 2006/0051738 A1 | 3/2006 | Zweig | |
| 2008/0066305 A1* | 3/2008 | Wang et al. | 29/846 |
| 2008/0180673 A1 | 7/2008 | Sampas et al. | |
| 2008/0237040 A1 | 10/2008 | Wessel | |
| 2009/0145753 A1 | 6/2009 | Yang et al. | |
| 2010/0012490 A1 | 1/2010 | Hsu | |
| 2010/0015006 A1 | 1/2010 | Hsu | |
| 2010/0021342 A1 | 1/2010 | Joseph et al. | |

* cited by examiner

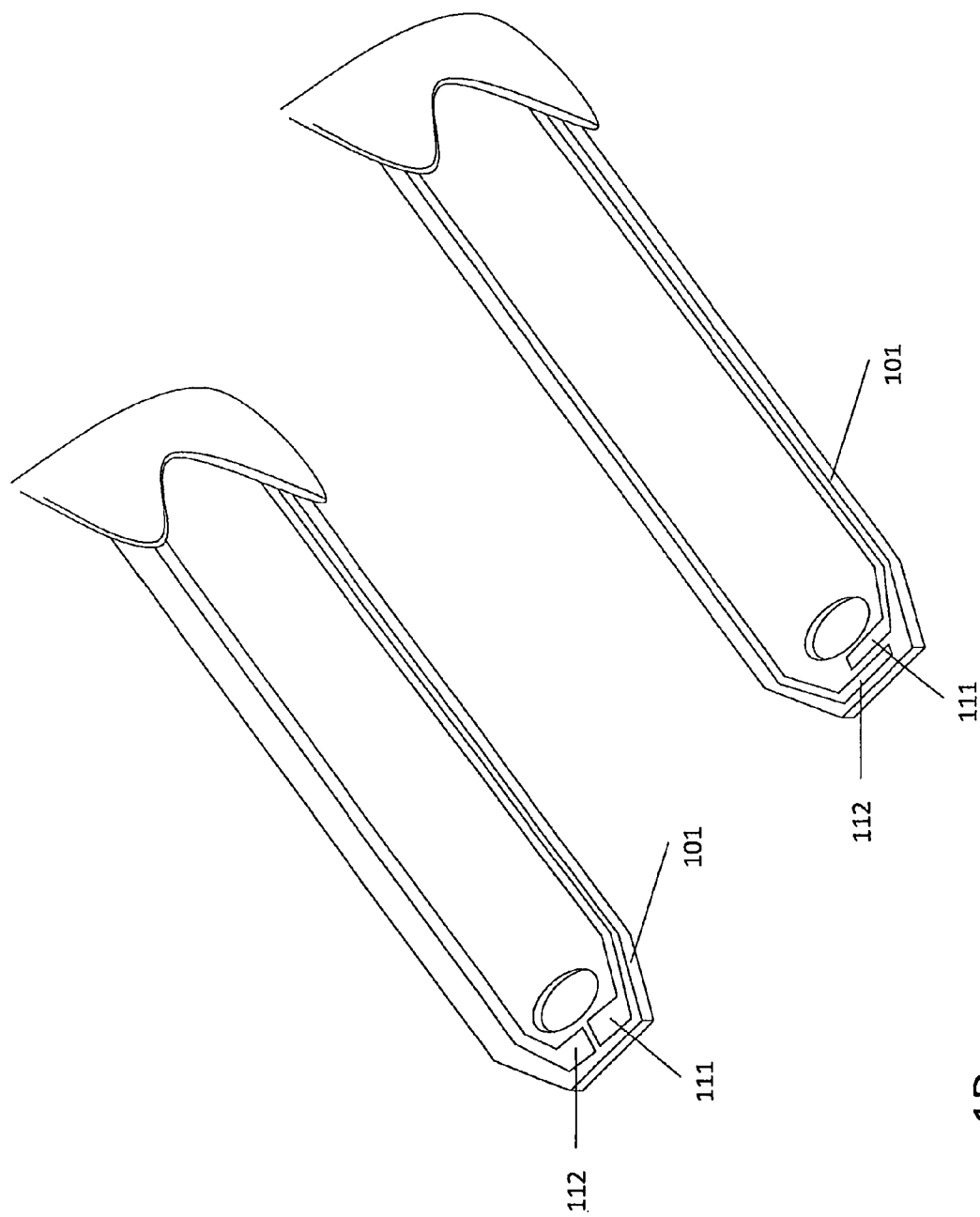

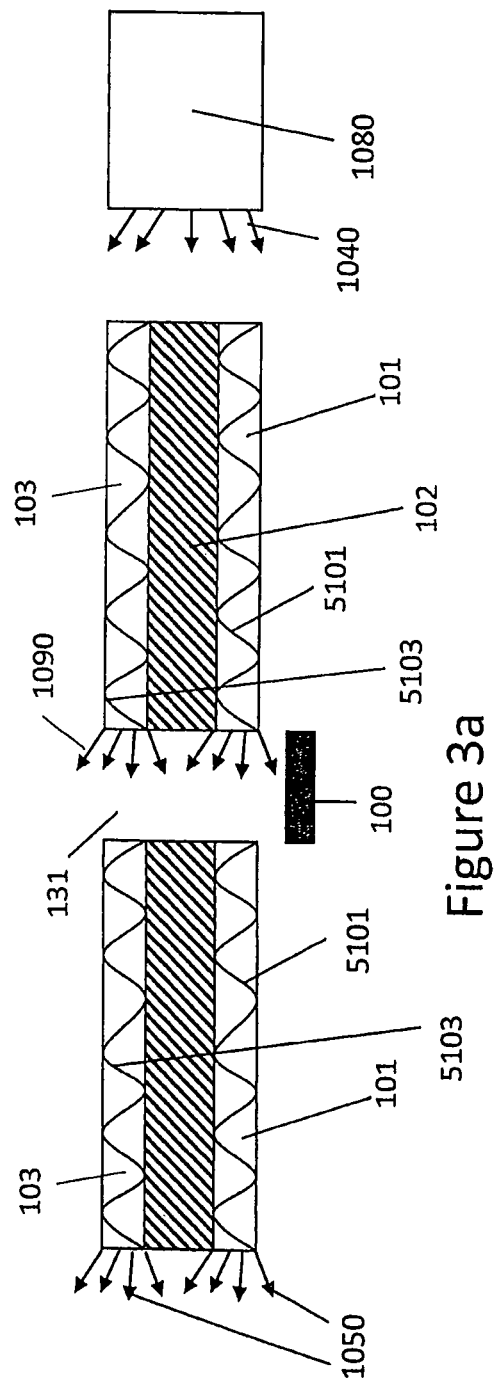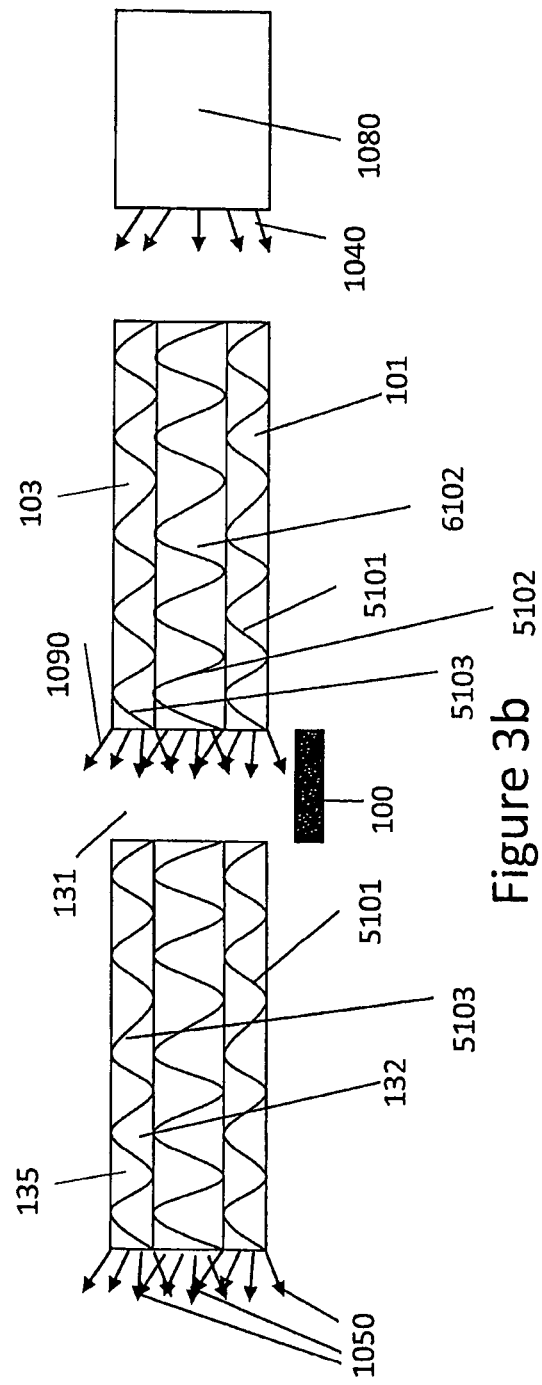
Figure 3a
Figure 3b

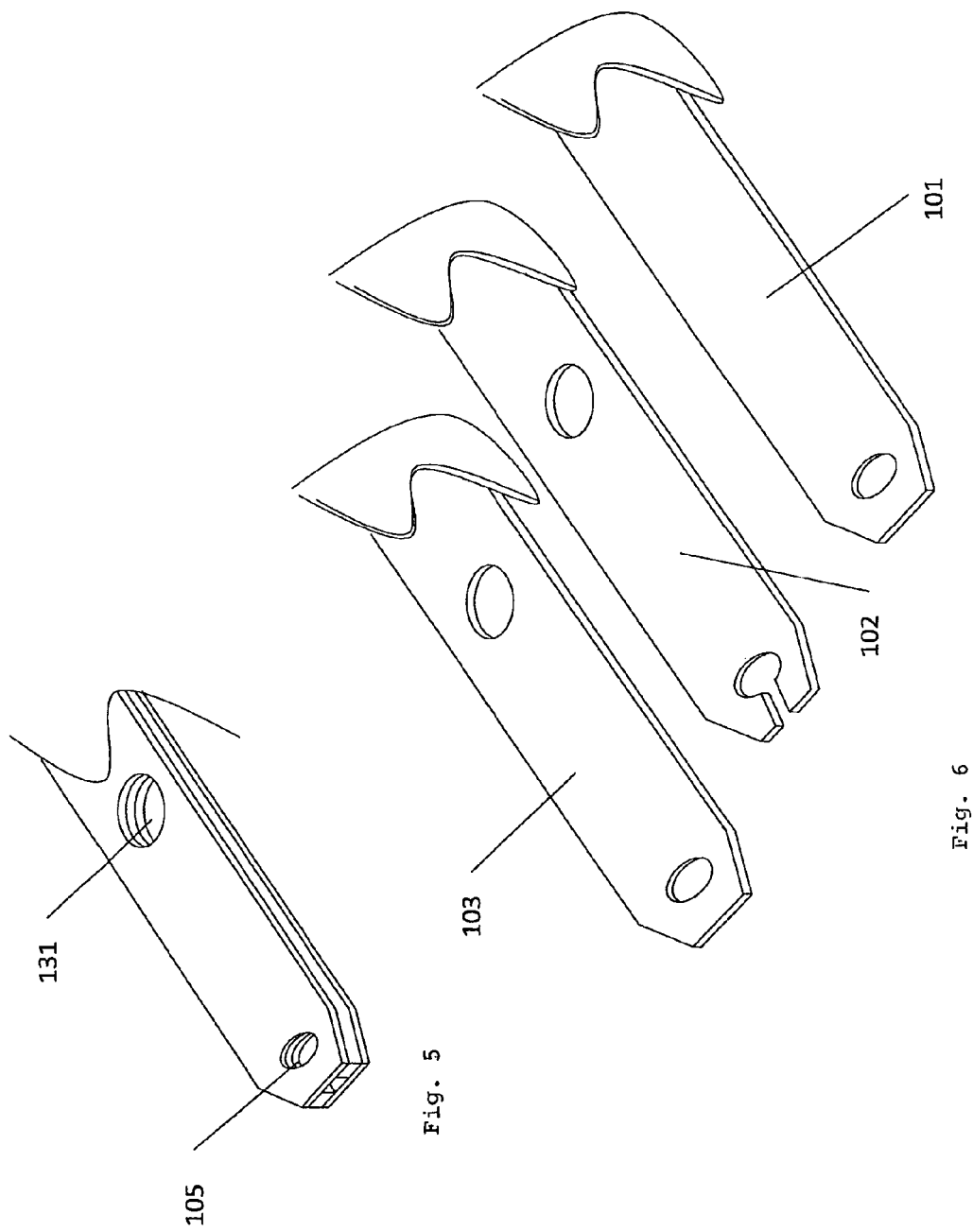

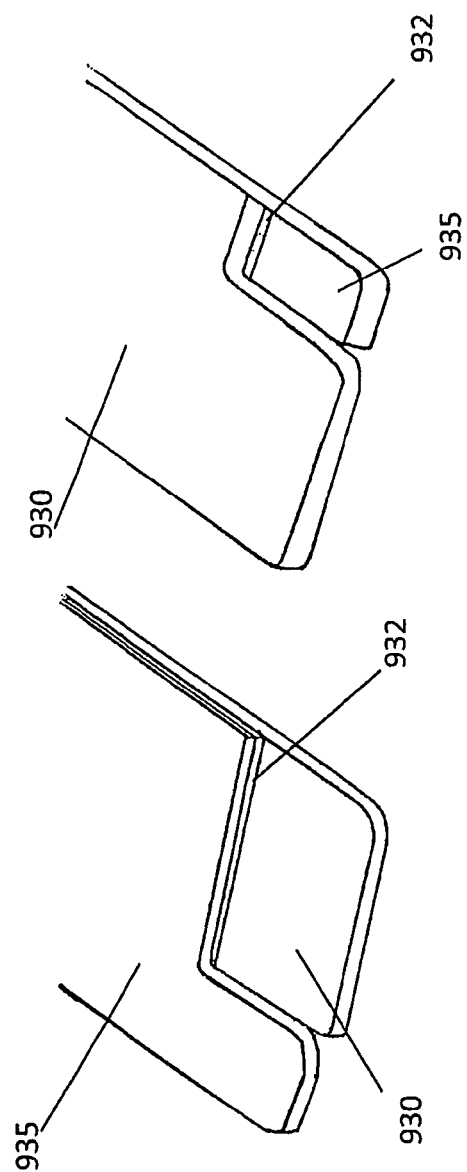

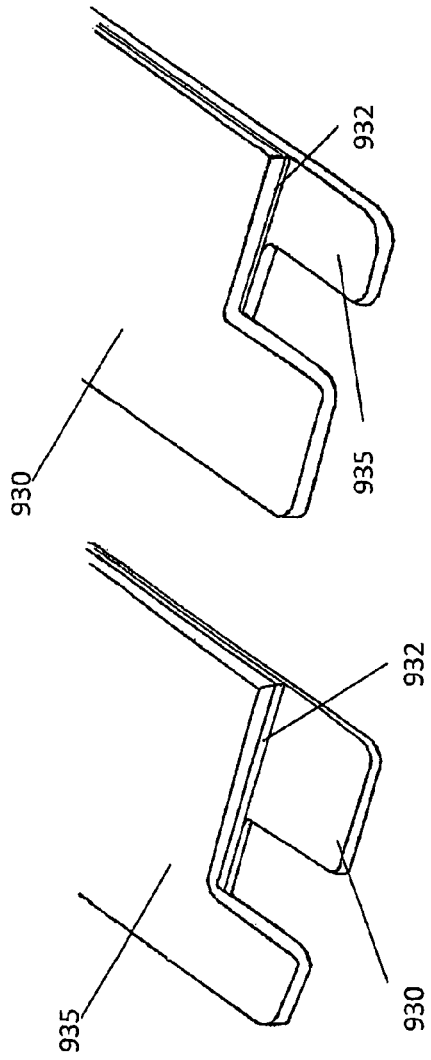
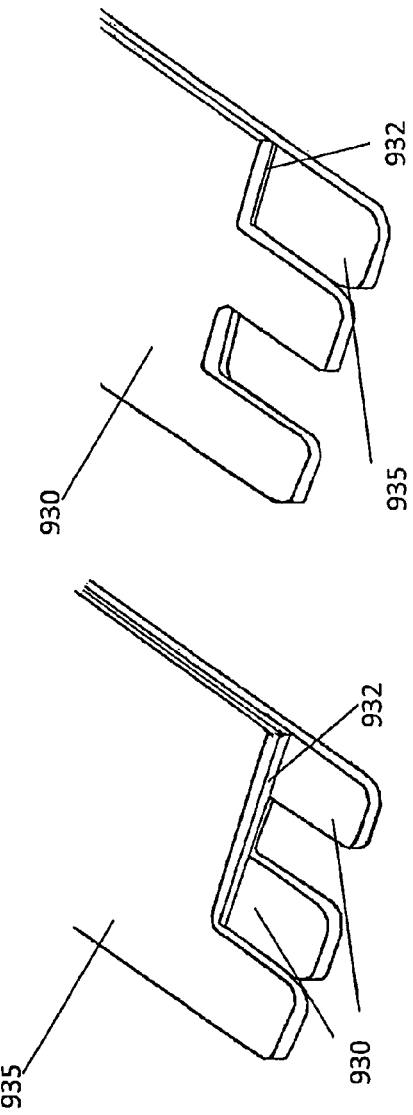
Figure 10A  Figure 10B  Figure 11A  Figure 11B

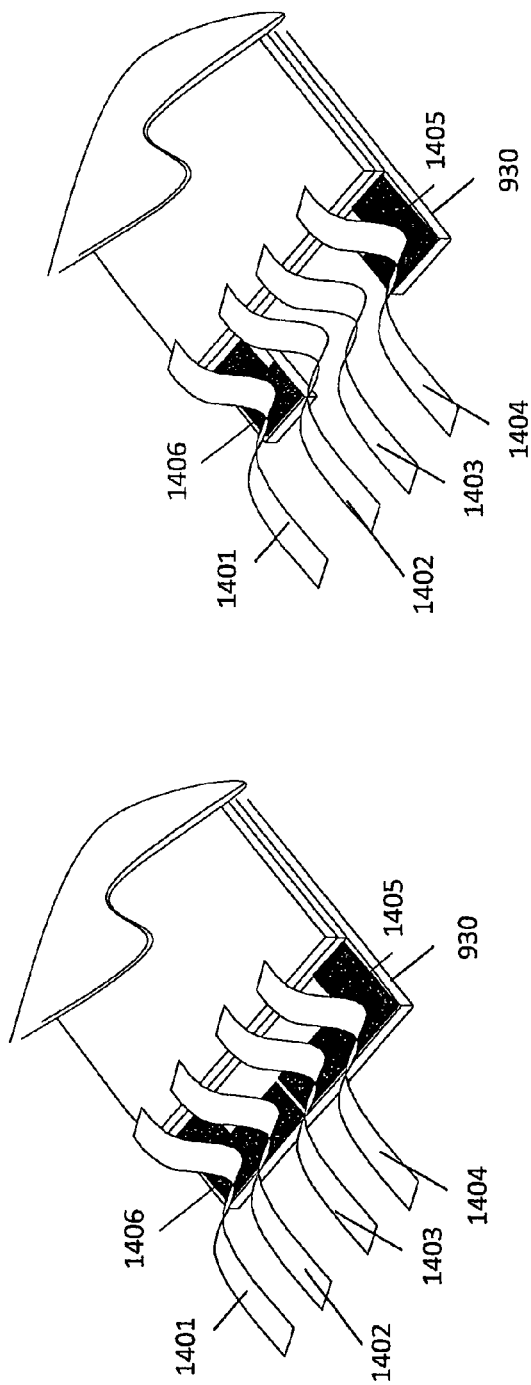
Figure 14g
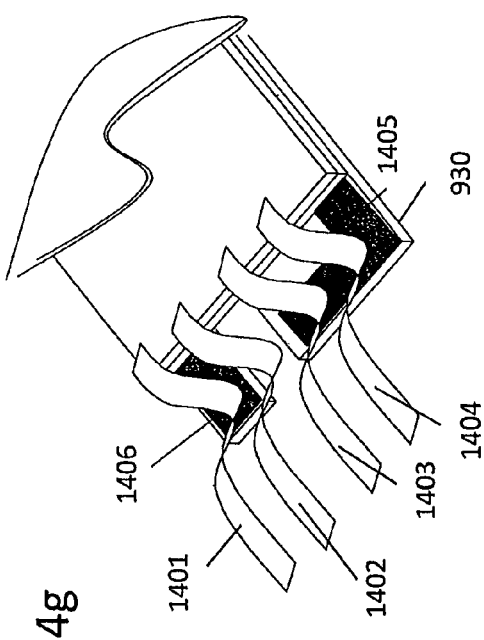
Figure 14h
Figure 14i

ANALYTE TEST STRIP AND ANALYTE METER DEVICE

RELATED APPLICATIONS

The present application is non-provisional application of and claims priority to U.S. Provisional Patent Application Ser. No. 61/362,229 filed on Jul. 7, 2010.

BACKGROUND OF THE INVENTION

The present invention relates to analyte test strips and meter devices used with these test strips. The invention also relates to health monitoring.

Test strips, such as those used in the current invention, are used to measure the amount of certain analytes in a biological sample, generally using electrochemical reactions. Test strips are well known to one of ordinary skill in the art and are described, for example, in U.S. Pat. Nos. 5,352,351; 5,565,085; and 5,628,890, and US Pat. Pub. 2005/0258035. All references cited in the present disclosure are incorporated herein by reference for all purposes. Small disposable electrochemical test strips are frequently used in the monitoring of blood glucose by diabetics. The test strip is combined with a sample such as blood before or after insertion in a reusable meter, which contains the mechanisms for detecting and processing an electrochemical signal from the test strip into an indication of the presence/absence or quantity of the analyte determined by the test strip. See U.S. Pat. No. 7,344,626 which is incorporated herein by reference.

Because some test strips vary from batch to batch, some models require the user to enter in a code found on the vial of test strips, or insert a chip that comes with the test strip. By entering the code or inserting the chip into the glucose meter, the meter will be calibrated to that batch of test strips. However, if this process is carried out incorrectly, the meter reading is quite inaccurate. The implications of an incorrectly coded meter can be serious for patients actively managing their diabetes. For miscoded meters, the probability of making an insulin dose error of 2 units is 50%. The probability of making an insulin dose error of 3 units is 24%, compared to 0.49% when using a no coding meter. (*Significant Insulin Dose Errors May Occur if Blood Glucose Results are Obtained from Miscoded Meters*, Charles H. Raine III, et al., 1 J. OF DIABETES SCIENCE AND TECH. 205 (March 2007). This places patients at increased risk of hypoglycemia. In order to reduce user error and decrease testing time, some test strips are now "no-code." This is done by designing the test strips such that they communicate with the meter and transmit calibration information with no need for user interaction. See, e.g. US Pat. Pubs. 2008/0237040 and 2005/0258035, which are incorporated herein by reference.

SUMMARY OF THE INVENTION

The present invention concerns use of a test strip with an incorporated optical waveguide and structures for deflecting the light (for example, apertures punched through at least a portion of the optical waveguide and/or indentations into at least a portion of the waveguide) to allow light to exit through a surface of the test strip and be detected by a photodetector. The deflecting structure can be created in varying patterns and positions, allowing the detected light to be interpreted as an indication of certain characteristics of the test strip. This can be used to encode information onto the test strip, such as the calibration code (e.g. thereby making the test strip a no-code test strip), the type of analyte to be detected, manufacturer's identification, or regional identification.

The invention also provides a novel strip geometry that is used with a strip port connector (SPC) of a meter for testing analytes that utilizes notched strip geometry to enable the creation of multiple configurations of a strip after initial manufacture.

Patterns of a plurality of deflecting structures (or "deflectors") or a combination of deflectors with notching at the electrical connection end are used to indicate more complicated characteristics, or multiple types of characteristics.

The invention provides a method for determining a characteristic of the above test strip. Light is cast/directed into the optical waveguide at the first end, then emitted from the deflector(s), and detected at least one photodetector, allowing determination of at least a characteristic of said test strip.

BRIEF DESCRIPTION OF THE DRAWINGS

FIGS. 1A, 1B, 1C, 1D, and 1E are perspective views of test strips with apertures in the top layer.

FIGS. 3A and 3B are cross-sectional views of an embodiment of the strip.

FIG. 5 is a perspective view of another embodiment of the test strip.

FIG. 6 is an exploded view of a test strip showing possible layers of the test strip of FIG. 5.

FIGS. 9A-B show top and bottom perspective views of possible-parent-notching patterns of the electrical connection end of the same test strip.

FIGS. 10A-B show top and bottom perspective views of one possible-child-notching pattern of the electrical connection end of the test strip of FIG. 9A-B.

FIGS. 11A-B show top and bottom perspective views of a second possible-child-notching pattern of the electrical connection end of the test strip of FIG. 9A-B.

DETAILED DESCRIPTION OF THE INVENTION

Figure 1A:
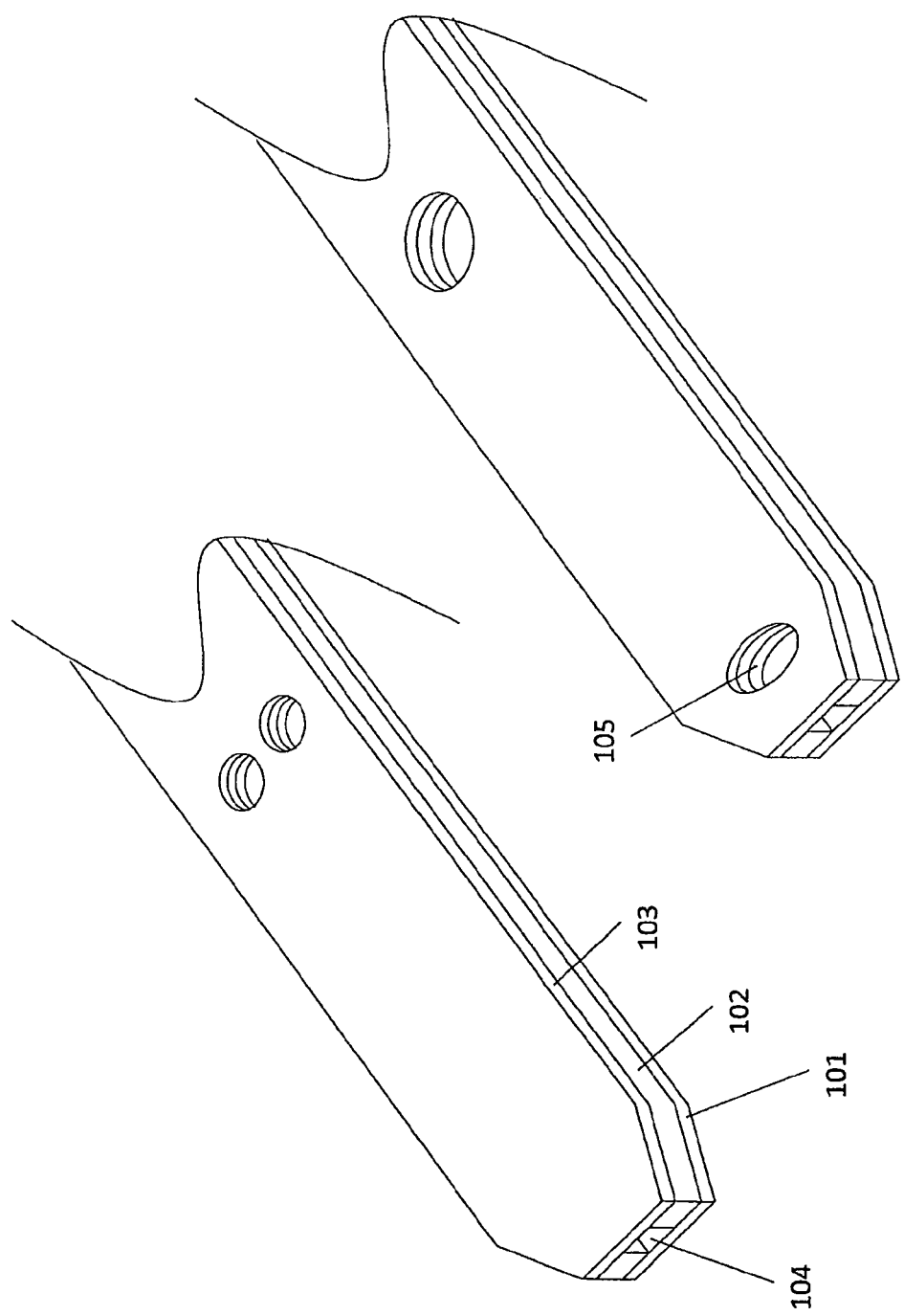

The present invention concerns use of a test strip with an incorporated optical waveguide and deflectors placed in at least a portion of the path of the light in the optical waveguide to allow light to exit through a surface of the test strip and be detected by a photodetector. The deflector can be created in varying patterns and positions, allowing the detected light to be interpreted as an indication of certain characteristics of the test strip. This can be used to make the test strip a no-code test strip, to indicate the type of analyte to be detected, to indicate regional identification, to indicate authenticity, or to indicate brand and/or manufacturer.

The invention also provides a novel strip geometry that is used with a strip port connector of a meter for testing analytes that utilizes notched strip geometry to enable the creation of multiple configurations of a strip after initial manufacture and multiply the number of configurations when used in combination with deflectors.

DEFINITIONS

As used in the specification and claims of this application, the following terms are used and should be understood as follows:

"Array" means a configuration with a number of elements grouped in a pattern, for example, in relation to each other (e.g. in rows, columns, circular patterns, a line, a cross shape, and/or so on.

"Aperture" means an opening, such as a hole, gap, or slit through which light can pass. It is of any shape, including simple shapes, such as a circle or square, or a more complicated polygon or a picture. It can extend through the entire strip or just part of the strip, so long as it is shaped and positioned to allow at least a portion of the light traveling in the wave guide exit out of itself.

"Deflector" means a structure that deflects electromagnetic waves (e.g. light) in a direction different from the direction in which it was traveling before it encountered said structure. Such structures can be physical embodiments such as apertures, holes, indentations, light scattering particles, and/or light absorbing particles; or can be optically-relevant embodiments such as employing materials of different refractive index or different densities, creating material compositions that act as lenses to focus, direct, bend, or deflect light. In preferred embodiments the deflector will deflect light so as to cause it to exit a test strip so it can be detected by a photodetector.

"Photodetector" means an instrument or element able to detect light. The photodetector merely senses any presence of light or distinguishes between varying amounts or wavelengths of light. This includes photoresistors or Light Dependent Resistors (LDR) which change resistance according to light intensity, photovoltaic cells or solar cells which produce a voltage and supply an electric current when illuminated, photodiodes which operate in photovoltaic mode or photoconductive mode, photomultiplier tubes containing a photocathode which emits electrons when illuminated, the electrons are then amplified by a chain of dynodes, phototubes containing a photocathode which emits electrons when illuminated and in general behaves as a photoresistor, phototransistors incorporating one of the above sensing methods, optical detectors that are effectively thermometers, responding purely to the heating effect of the incoming radiation, charge-coupled devices (CCD), such as are used to record images in astronomy, digital photography, and digital cinematography, and LEDs reverse-biased to act as photodiodes. The photodetector is a single detector, able to detect light from one source, an array of detectors, able to read numerous sources, or, for example, a CCD able to read a range of sources.

"Photogenerator" means a source of light. The light can be generated from, for example, a light-emitting diode (LED), fluorescence, phosphorescence, incandescence, halogen, chemoluminescence or electroluminescence.

"Strip port connector" or "SPC" is the portion of an analyte measuring instrument that interacts with a test strip. Usually, this portion has electrical connections that interact with electrode contacts on the test strip. The strip port connector may have a photogenerator incorporated in its structure, or it may have a guide, such as an opening, a lens, or an optically transmissive structure connected to a light source within the analyte meter, which facilitates light entering into the waveguide in the test strip.

A "waveguide" is a structure that guides electromagnetic waves, preferably electromagnetic waves in the optical spectrum. A waveguide can be a portion of the strip that allows at least partial transmission of electromagnetic waves generally in one direction. The simplest case is a rectangular waveguide, which is formed when the guiding layer of a slab waveguide is substantially restricted in both transverse directions rather than just one.

The term "punch" as used in the specification and claims of this application refers to the act of deforming a portion of a sheet of material in a direction substantially perpendicular to the major surface. The deformation can be an indentation on a surface, a cut through a portion of the material, a cut through all of the material, or a protrusion out of the surface. The term "substantially" in this case recognizes that there are slight manufacturing deviations from absolutely perpendicular, but that these should be preferably minimized. Punching may be performed using a die cutting apparatus or other apparatus that physically cuts the layers into the desired shape or by an embossing type of apparatus that creates indentations into or protrusions on a surface. Laser cutting can be employed where heat generation and/or evolution of volatiles is not a concern. Chemical etching through the materials might also be employed.

The term "characteristics" refers to the certain information and properties associated with the test strip. This includes what type of analyte the tests strip measures, calibration algorithms and/or constants used (for example to create a no-code test strip). It also includes providing regional identification or showing that the strip is not a counterfeit and made by an authorized manufacturer. It is also used to determine proper alignment, for example, preventing a test strip from being inserted upside down or not completely inserted. It is possible that a test strip possesses a combination of these characteristics, and it is useful to transmit a plurality of these characteristics with the present invention.

"Alignment" of deflectors, when used, means that two or more deflectors may be aligned such that at least a portion of light cast through one deflector is able to exit the other deflector(s).

"Alignment" of a test strip means that the strip is properly inserted into an analyte test meter. The strip is not inserted upside down, it is fully inserted and it is in correct electrical contact with the strip port connector.

A "test strip receiving area" is the portion of an analyte testing meter that guides a test strip to the strip port connector. It has an open insertion point at one end, and the strip port connector is at the other end. The receiving area should be shaped to guide the test strip to be inserted in the proper alignment.

The "electrochemical test cell" is the portion of the test strip where a sample, usually blood, is drawn into. This area comprises the reagents and electrodes necessary to perform the electrochemical reaction used in determining the analyte in a sample.

The "electrical connector" is the portion of the test strip that interacts with the strip port connector of the analyte test meter. It provides electrical connections that connect the electrochemical cell to the analyte test meter.

"Tabs" refers to structures on a test strip created by a manufacturing process of creating configurations of sections of the electrical connector end of a test strip, for example, as shown in FIGS. 9A-B. These sections should be at least partially offset and not completely overlapping, thereby allowing for notching of these structures after both top and bottom layers of the test strip have been assembled. Tabs need not be present on both surfaces of a strip; it is sufficient to have a tab only on one surface, though it is preferable to have tabs on both surfaces.

"Notching" refers to the manufacturing process of creating "child" configurations of test strip ends from "parent" configurations. The tabs created during production are cut, punched, or physically altered to create a new geometrical configuration (including for example, unique electrical contact positions or unique physical features). This is used to indicate characteristics of the test strip.

"Not contiguous" means there is no air connection between the deflector and a venting hole connected to the electrochemical cell.

Method for Determining Characteristics of a Test Strip:

The present invention provides a method of detecting characteristics of a test strip by using a test strip with an incorporated optical waveguide and a deflector punched into the waveguide so that at least a portion of the light introduced into the test strip waveguide when the strip is inserted into an apparatus exits through a surface and is detected at a photodetector. Detection of light at this photodetector correlates to at least one characteristic of the test strip.

An example of this method is shown in FIGS. 3A and 3B; in both FIG. 3a and FIG. 3b, the test strip example is illustrated by three layers of material. The top and bottom layers 101, 103 act as waveguides in both examples. In FIG. 3a, the middle layer 102 is a spacer layer that is not optically transmissive (for example, it can be a layer of opaque PET with adhesive on both sides). Thus, in this example, only other outer layers 101 and 103 act as waveguides transmitting light 5101 and 5103. In FIG. 3b, the middle layer 6102 is optically transmissive (for example, it can be a layer of transmissive PET with adhesive on both sides). Thus in this example, all three layers 101, 102, 103 act as waveguides. In both of these figures, light 1040 is generated at a photogenerator 1080, directed into the optical waveguides 101, 103 (and additionally 6102 in the case of FIG. 3b) where it travels to the deflector 131, at least partially exits the waveguide 101, 103 (and 6102 in the case of FIG. 3b), and is detected by the photodetector 100.

Figure 13:
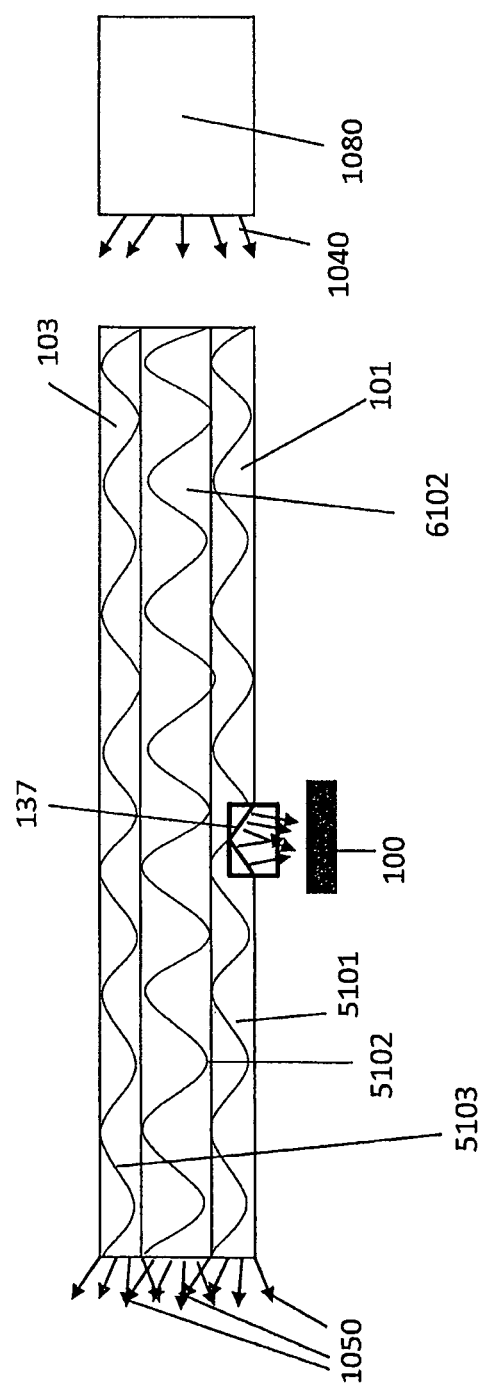
FIG. 13 shows a cross section of the strip indicating waveguides and light emitted at the front end of the strip and the use of indentation deflector to deflect light towards the photo detector.

In the embodiment shown in FIG. 13 light 1040 generated by photogenerator 1080 is directed into and travels along 5101, 5102, 5103 waveguides 101, 6102, 103, and is emitted 1050 at the front end of the strip. Light is also emitted at indentation deflector 137 which deflects light towards the photo detector 100 to be detected thereat.

An electrochemical test strip has electrical contacts at one end (that interface with a meter's strip port connector), an electrochemical test cell at the opposite end, a waveguide extending between the two, and a deflector in the waveguide, wherein light can exit the waveguide via the deflector. Test strips used in this method are described in further detail below, however, any test strip with a waveguide and at least one deflector can be used. Furthermore, it will be appreciated that a non-electrochemical test strip may also be used with the invention (for example, a photometric or colorimetric test strip which relies on optical measurements of the chemical reaction).

Characteristics of the test strip which may be useful for tracking and encoding include what type of analyte the test strip analyzes and calibration information to create a test strip that the user does not have to manually code. It can also provide regional identification, or it can show that the strip is not a counterfeit and made by an authorized manufacturer. It can also be used to determine proper alignment, for example, preventing a test strip from being inserted upside down or not completely inserted.

One meter apparatus used in the method has a light source and a photodetector. The light source of the apparatus is situated so that, when the test strip is inserted into the apparatus, light will be directed into the waveguide. The light travels through the waveguide, at least partially exiting at the deflector, where it is detected by a photodetector.

This apparatus is an analyte test meter which comprises electronics and a strip port connector (for connection to an analyte test strip) for assessing a concentration of analyte in a sample or can be an apparatus solely used to evaluate the strips themselves (for example, an apparatus used during manufacture to ensure the test strip has been marked properly and directs light from the waveguide as it should).

This method can also be used with a test strip possessing a plurality of deflectors, creating a pattern. This pattern can be interpreted as an indication of a characteristic with multiple variables, or of a plurality of characteristics.

In addition to a test strip with deflectors, in another embodiment, a test strip with variable notching patterns can also be used. A parent configuration is constructed, such as shown in FIGS. 9A-B. Characteristics of the strip are determined, and the tabs can be notched to indicate characteristics, as shown in FIGS. 10A-11B. The apparatus is able to distinguish between these varying notching patterns (for example by detecting the presence or absence of electrical connections using the SPC), and a characteristic of the strip can be determined. This notching pattern can be used in combination with deflectors, or independently.

Test Strips:

The present invention provides a test strip comprising deflectors that can be interpreted as an indication of characteristics of the strip. For example, in one embodiment, the deflectors of the test strip are interpreted such that the test strips only work with certain types of meters or meters with designated geographic regions. In another example embodiment, deflectors in the test strip are interpreted as indications of different calibration settings and the test strip indicates a calibration equation or code associated with it, thus allowing the end user to interact with it as though it were a no-code strip.

In certain embodiments, as shown in FIG. 1A, FIG. 5, and FIG. 6 test strips are constructed with waveguide(s) 101 and/or 103 and deflector(s) (e.g. aperture(s), 131 in FIG. 5, toward rear of strip) formed in the waveguide(s) 101 and/or 103. The deflector(s) deflects light directed into the waveguide(s) 101 and/or 103 and allow light to escape the test strip. In this embodiment, the top (103) and bottom (101) layers of the strip act as the waveguides, and the deflector is an aperture through the entire strip.

In a preferred embodiment, the transmission of light through the waveguide would be nearly perfect; however, varying amounts of transmission are contemplated, including transmission of at least 5%, 10%, 20%, 30%, 40%, 50%, 60%, 70%, 80%, 90%, 95%, and 98% of light. The light-transmitting section of the strip can also be fluorescent or phosphorescent, so that the strip lights up and is easy to see.

Figure 4:
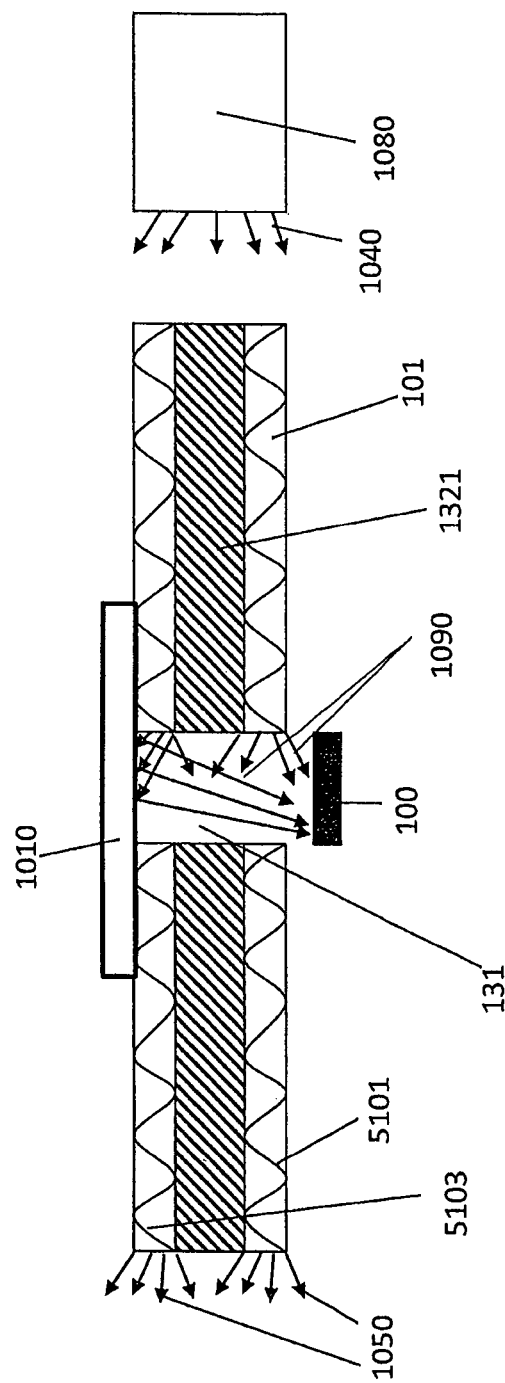
FIG. 4 is a cross-sectional view of another embodiment of the strip.

The waveguide can extend the entire length of the strip, with openings at both ends. Light 5101, 5103 passes along the length of the strip as shown in FIGS. 3a and 5101, 5102, 5103 as shown in FIG. 3b. In one embodiment, at least a portion of the traveling light can be emitted at the opposite end as shown at 1050. Deflectors 131 (in this example) are created by making a hole through the optical waveguide(s) 101, 103, and/or 102, such that light can exit out of it. If the test strip comprises a deflector that allows light to exit from the top and bottom of the strip (for example as shown in FIG. 3), a reflective material or surface 1010 can be optionally placed on the strip one side of the deflector 131 (for example as shown in FIG. 4) such that it directs light back toward a photodetector 100. This has the benefit of generating a larger signal at the photodetector 100. In FIG. 4, the strip does not have a waveguide in the middle layer; however, it is understood that this concept can be used with strips that have waveguides in multiple layers. In an alternative embodiment, a reflective material can be placed on the interior of the analyte test meter such that it directs at least a portion of the light back towards a photodetector; such a reflective material or surface can be part of the meter housing or part of the SPC itself. If the hole is not punched all the way through, the remaining layer can be constructed out of a reflective material, or a layer of reflective material can be added between the remaining layer and the optical waveguide, thereby directing light through the deflector.

Figure 12:
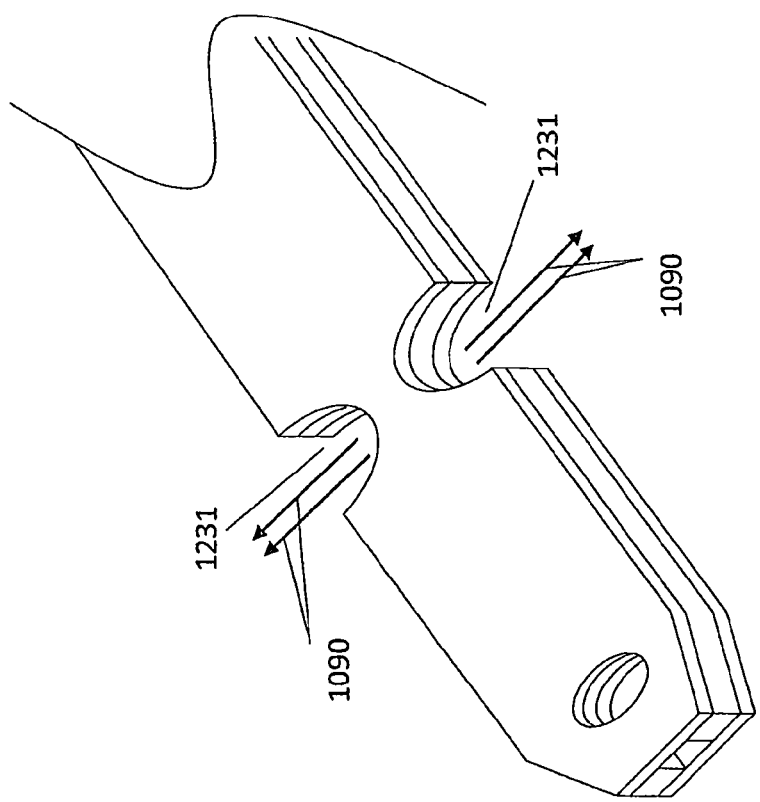
FIG. 12 shows an alternative configuration for apertures.

Alternatively, as shown in FIG. 12, deflectors 1231 can be created by punching a notch through the test strip so that light exits 1090 through the side, instead of the top or bottom.

Figure 2A:
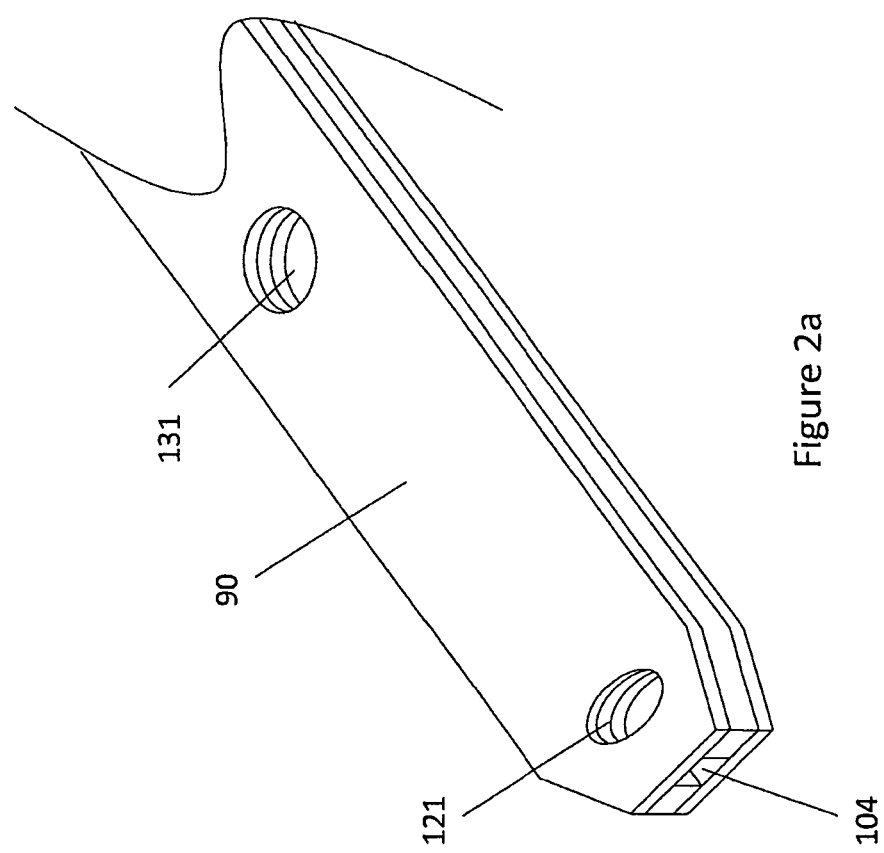
FIGS. 2A, 2B, 2C, and 2D are perspective views of test strips showing a variety of aperture configurations.
Figure 2B:
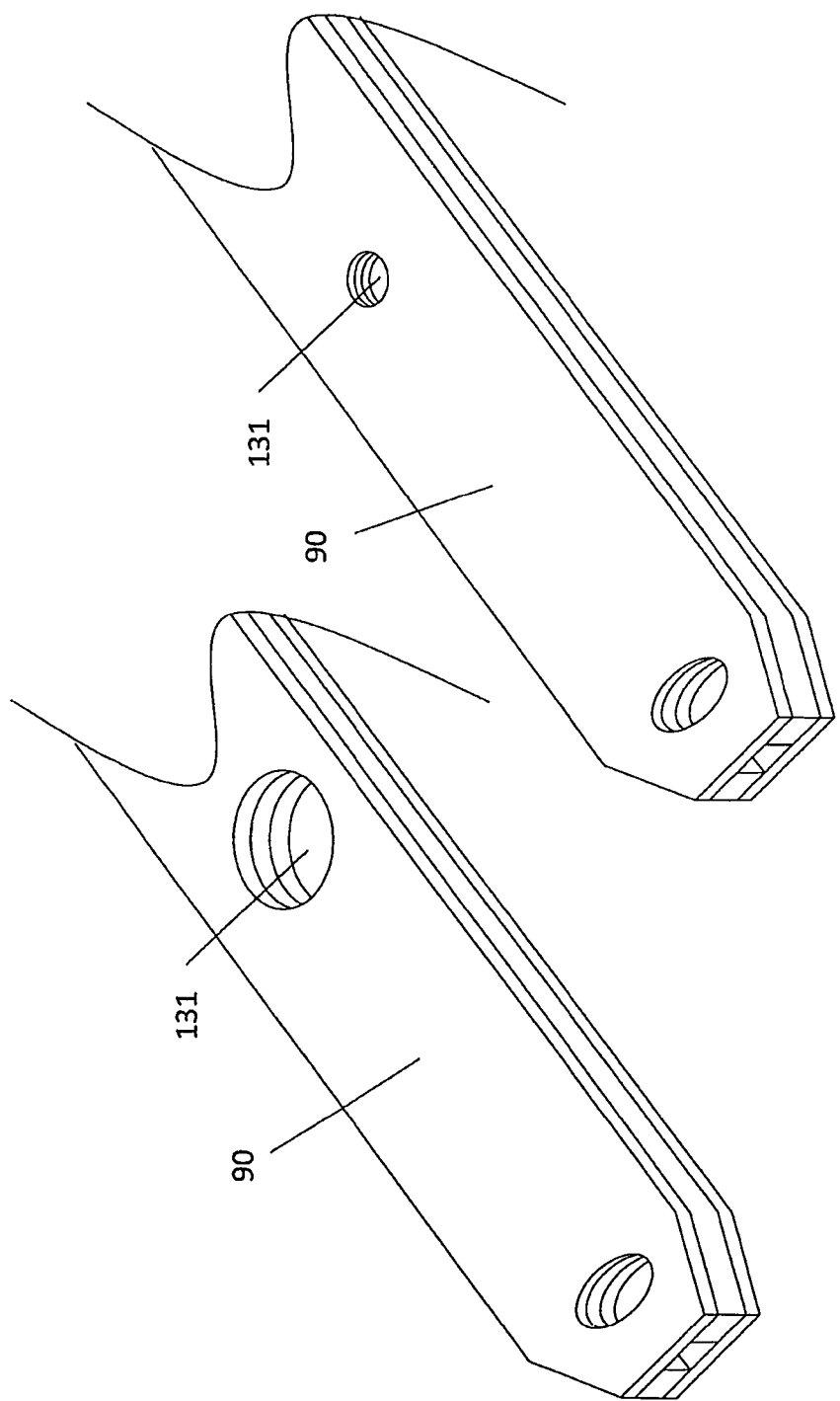
Figure 2C:
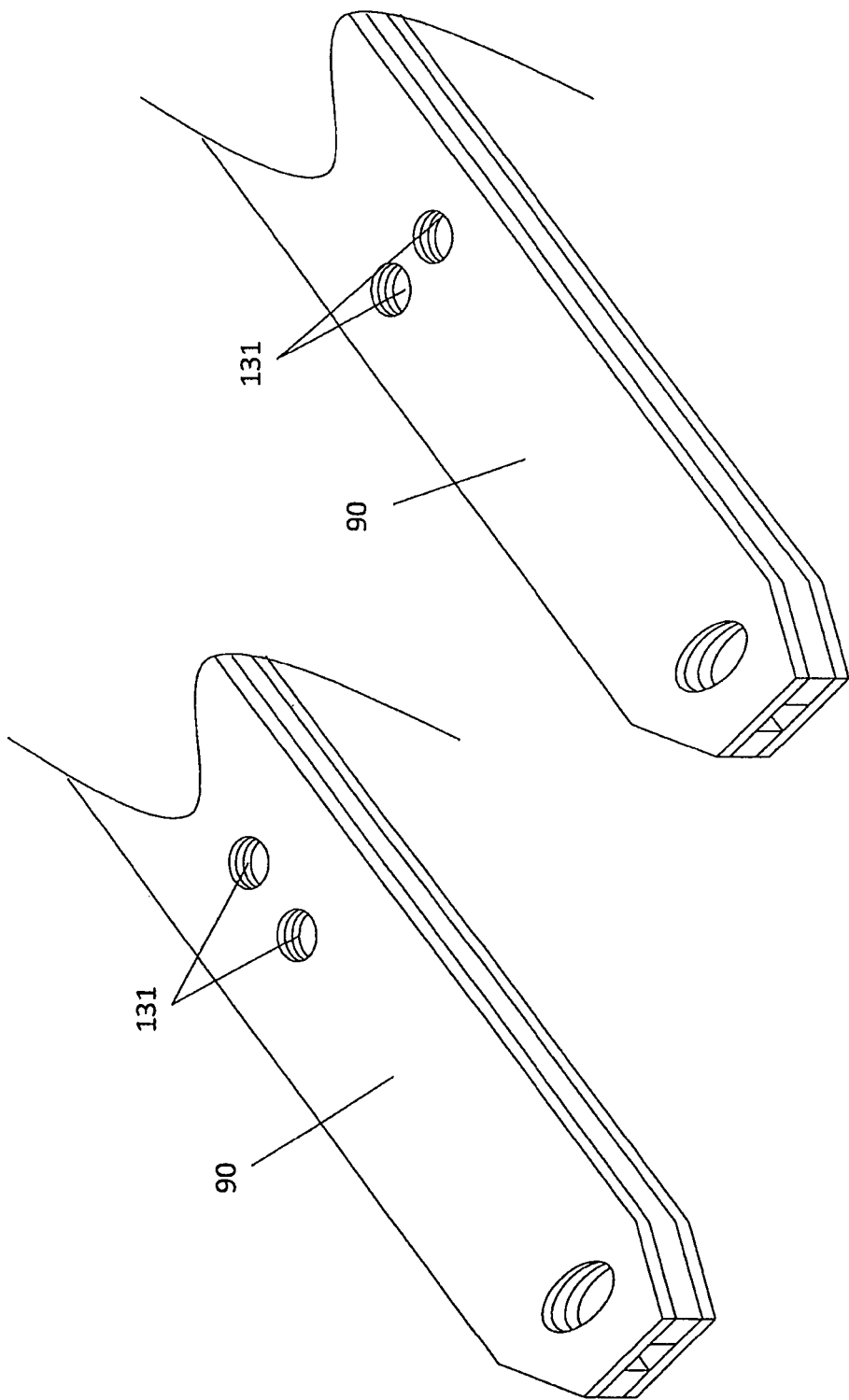

The deflectors 131 can be of varying dimensions, as shown in FIG. 2B. This changes the amount of light that exits the waveguide. Where a hole is used as a deflector, a larger hole lets more light escape and more light to reach the photodetector. A smaller hole allows less light to escape and less light to reach the photodetector. If a photodetector is used that is capable of distinguishing varying amounts of light, the varying amount of light can be used as an indicator of characteristics. Other ways of modulating the amount of light reaching the photodetector are known in the art, such as use of semi-transmissible material.

In addition, a pattern of deflectors 131, 731, 740, 741, 831, and 832 can be created, as shown in FIG. 2C, and FIGS. 7A-8. This pattern can be in a straight line, or in a two-dimensional array, with a multiplicity of rows and columns, or can be in any other geometric alignment (for example in a circular arrangement). For example, a base array of 2×2, 2×3, 3×3, 4×4, 3×4, or 5×5 is envisioned, where each position either has a deflector or does not. When creating an array of deflectors, one can view the pattern as a grid in which some positions are on and some positions are off. Each position where a deflector can be present may be associated with a separate photodetector; however, this is not a requirement. For example, if one photodetector (100) is situated in a position to receive light from two deflectors, then the presence of two deflectors will result in more light being captured by the photodetector, thereby giving a higher signal, than if only one photodetector were present. Thus, one can envision different configurations being detected by using multiple deflectors to vary the light signal instead of using deflectors of different sizes.

The test strip can combine deflectors in different patterns and sizes for a more complex scheme. Therefore, such an array has several possibilities at each position, such as no deflector, small deflector, or large deflector, thereby allowing at least three different configurations to be encoded in one location.

Figure 7A:
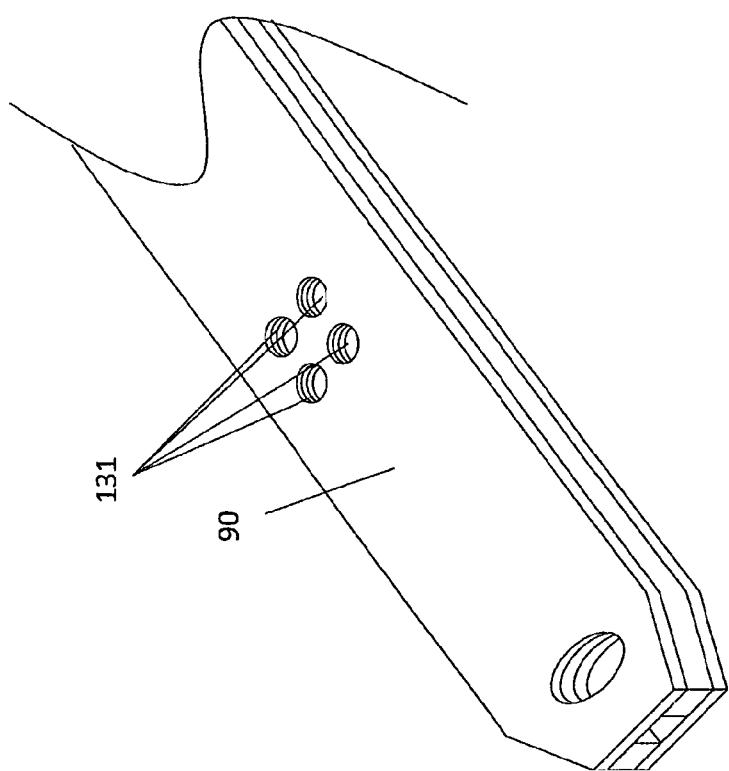
FIGS. 7A-D are top and bottom perspective views test strip embodiments of the present invention. The dotted lines in 7C and 7D indicate internal features.
Figure 7B:
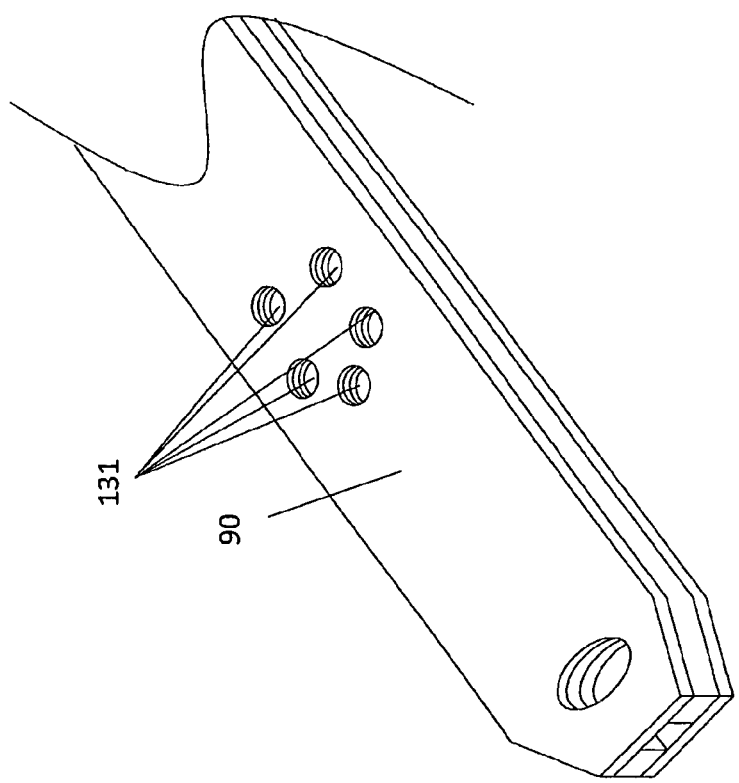
Figure 7C:
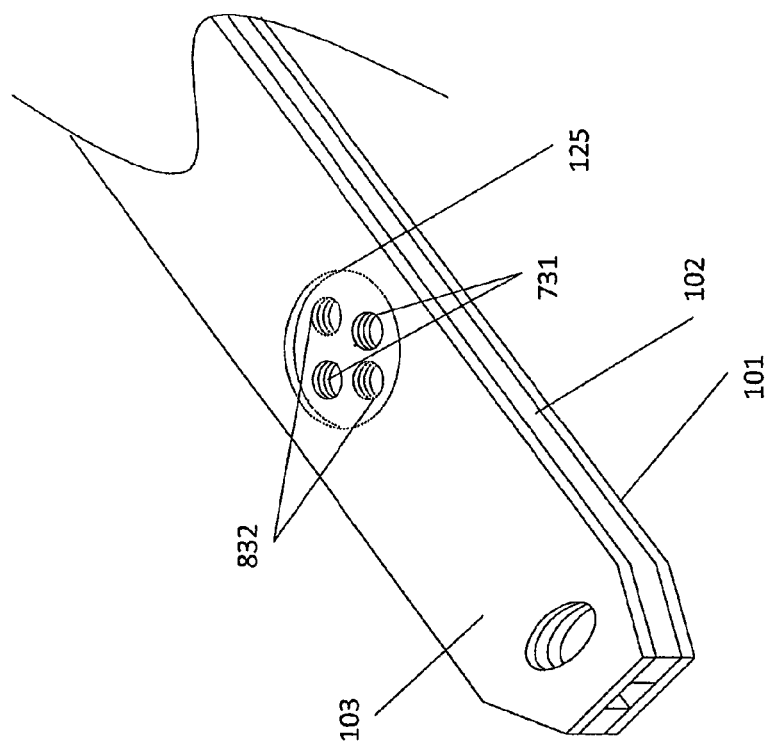
Figure 7D:
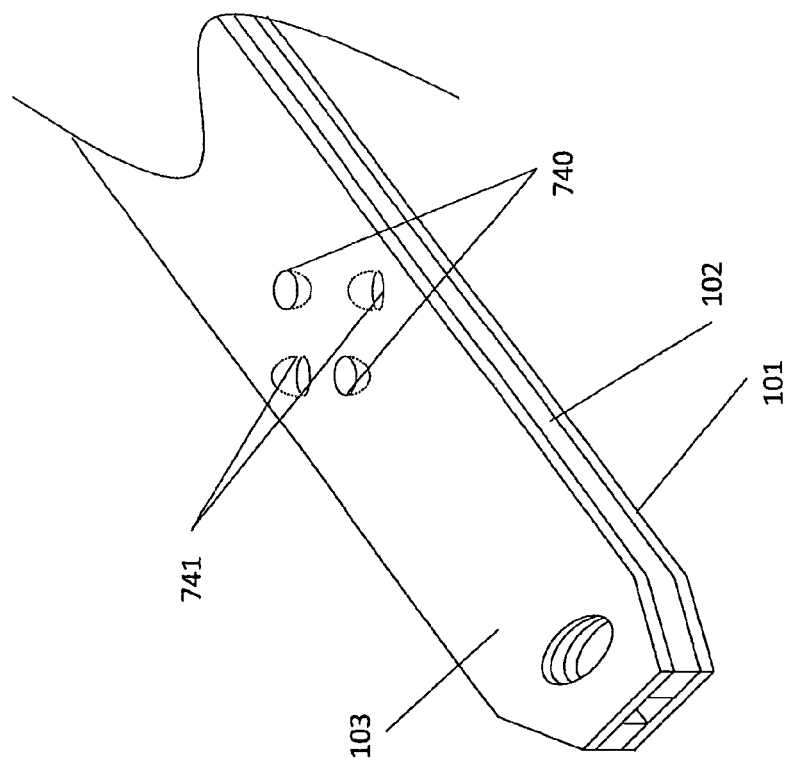
Figure 8:
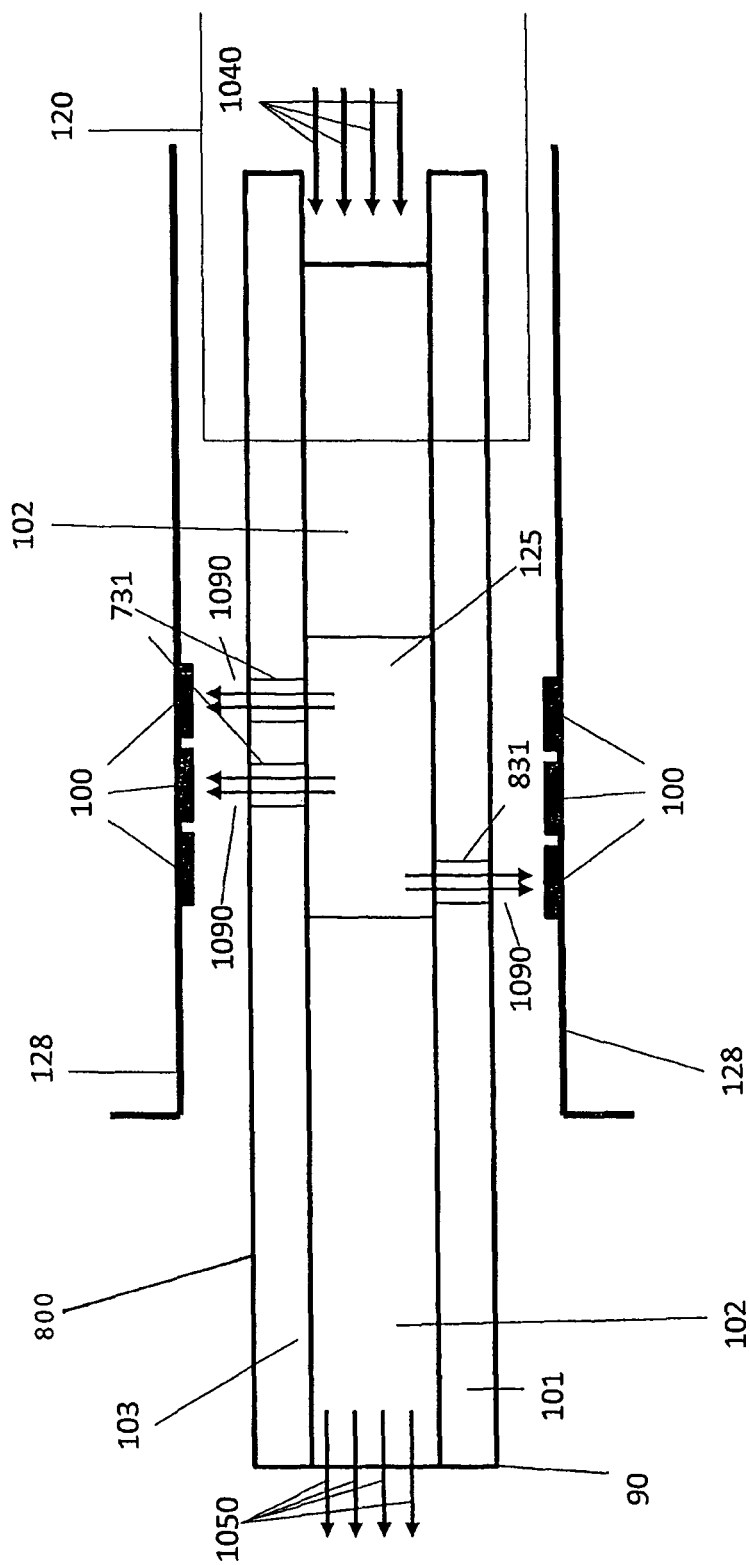
FIG. 8 is a cross sectional view of a test strip.

In another embodiment, a different deflector pattern can be used on the top layer 103 as compared to the bottom layer 101, as illustrated in FIGS. 7C, 7D and FIG. 8. In FIG. 7C, this is accomplished by creating a large aperture 125 through the middle layer, then creating one pattern of smaller apertures 731 in the top layer 103 and a second pattern 832 on the bottom layer 101. The middle layer 102 serves as a waveguide in this example; the top layer 103 and the bottom layer 101 both optionally serve as waveguides. In another example embodiment, as shown in FIG. 7D, the top layer 103 and the bottom layer 101 both serve as waveguides, whereas the middle layer 102 optionally serves as a waveguide. Here, the deflectors are indentations created in the waveguide layers instead of apertures. Indentations 740 are in the top layer 103, and indentations 741 are in the bottom layer 101. As can be seen in the example embodiments of both FIG. 7C and FIG. 7D, the location of the deflectors on the top and bottom of the strip need not match.

FIG. 8 shows how non-aligning deflectors may be monitored by the meter apparatus. Light 1040 enters the strip waveguide (in this example the waveguide is shown to be the middle layer 102). Middle layer large aperture 125, top layer apertures 731, and bottom layer aperture 831 are shown. Light 1090 exits the strip via the apertures (731 and 831) and is detected by photodetectors 100 in the meter apparatus 128. As can be seen, in this example, there are a total of six photodetectors (three facing each side of the strip) which allows a total of 64 unique configurations to be determined, assuming that each aperture allows approximately the same amount of light to exit if it is present and block approximately the same amount of light if the aperture is not present. This in effect serves as a binary encoding mechanism whereby each location of the deflector can be in an "on" state (deflector emitting light) or in the "off" state (deflector not emitting light). As can also be seen in FIG. 8, a portion of the entering light 1040 also can exit out the end 90 of the strip 1050. This has the benefit of illuminating the end 90 of the strip where the sample is to be placed, thereby increasing the visibility and usability of the system to the end user.

In addition to using the optical waveguide to transmit light to the deflector, in another embodiment, it can be used to illuminate the edges of the test strip, including the sampling end of the strip. If the optical waveguide extends all the way through the length of the test strip, light entering the strip at one end can at least partially exit the strip at the opposite end; furthermore, light can also partially exit along the side edges of the strip. See, e.g., US Pat. Pub. 2005/0258035 and JP Pat. Pub. H11-235196. In this way it is possible to illuminate the lanced area (the skin area that has been pricked to produce a drop of blood) so that the tip of the strip is readily guided to the location of the drop of blood to facilitate sample acquisition.

FIGS. 1A-E show schematic representations of a strip. In this example embodiment, the strip comprises an electrochemical cell. In this example, the strip is formed from a bottom layer 101, a middle layer 102, and a top layer 103. There is an electrochemical cell 104 which accepts a sample to be analyzed. It is apparent that strips which employ other methods of analytical detection (for example, optical detection such as photometry or colorimetry) are also within the scope of the invention disclosed herein and the electrochemical cell 104 may be a different type of assay/test space. An electrochemical test cell 104 is comprised of at least two electrodes and the necessary reagent system to perform the measurement assay. In the example case of glucose detection, the reagent can comprise a glucose-reactive enzyme such as glucose oxidase or glucose dehydrogenase. It will be appreciated that other reagent systems can be used with this invention by utilizing different reagent systems appropriate for the assay of the target analyte.

Figure 1B:
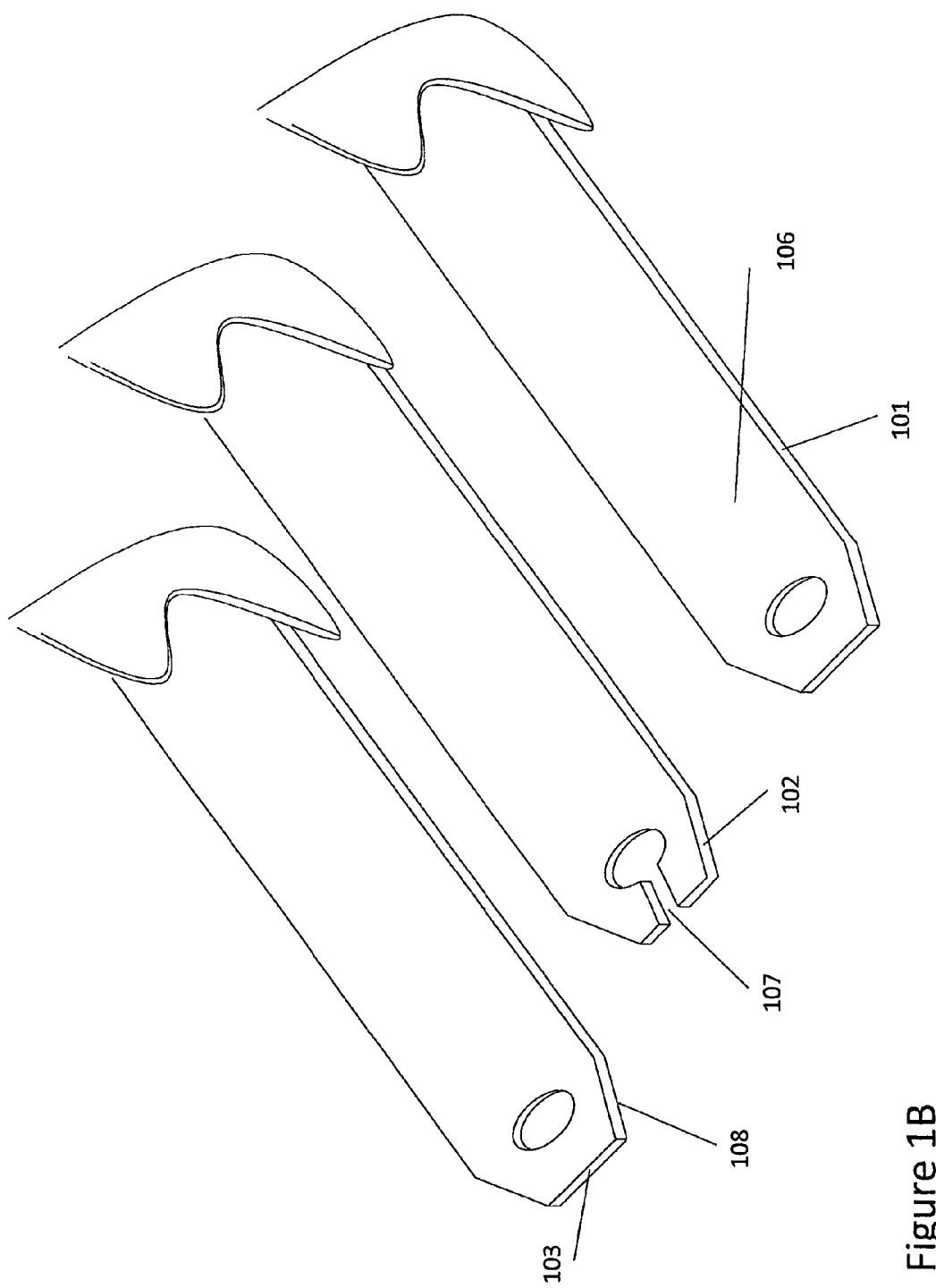

One method of constructing an electrode system for the electrochemical cell shown in FIG. 1B. Here, three layers of the example strip are shown in an exploded view. The assay space 104 shown in FIG. 1A is bounded by the bottom layer 101, the top layer 103 and the cut-out portion 107 in the middle layer 102. The bottom layer 101 comprises a conductive surface 106 on the side that faces up towards the assay space. The top layer 103 also comprises a conductive layer 108 on the side that faces down towards the assay space. The exposed portions of the conductive layers 106 and 108 comprise two electrodes of the electrochemical cell.

Figure 1C:
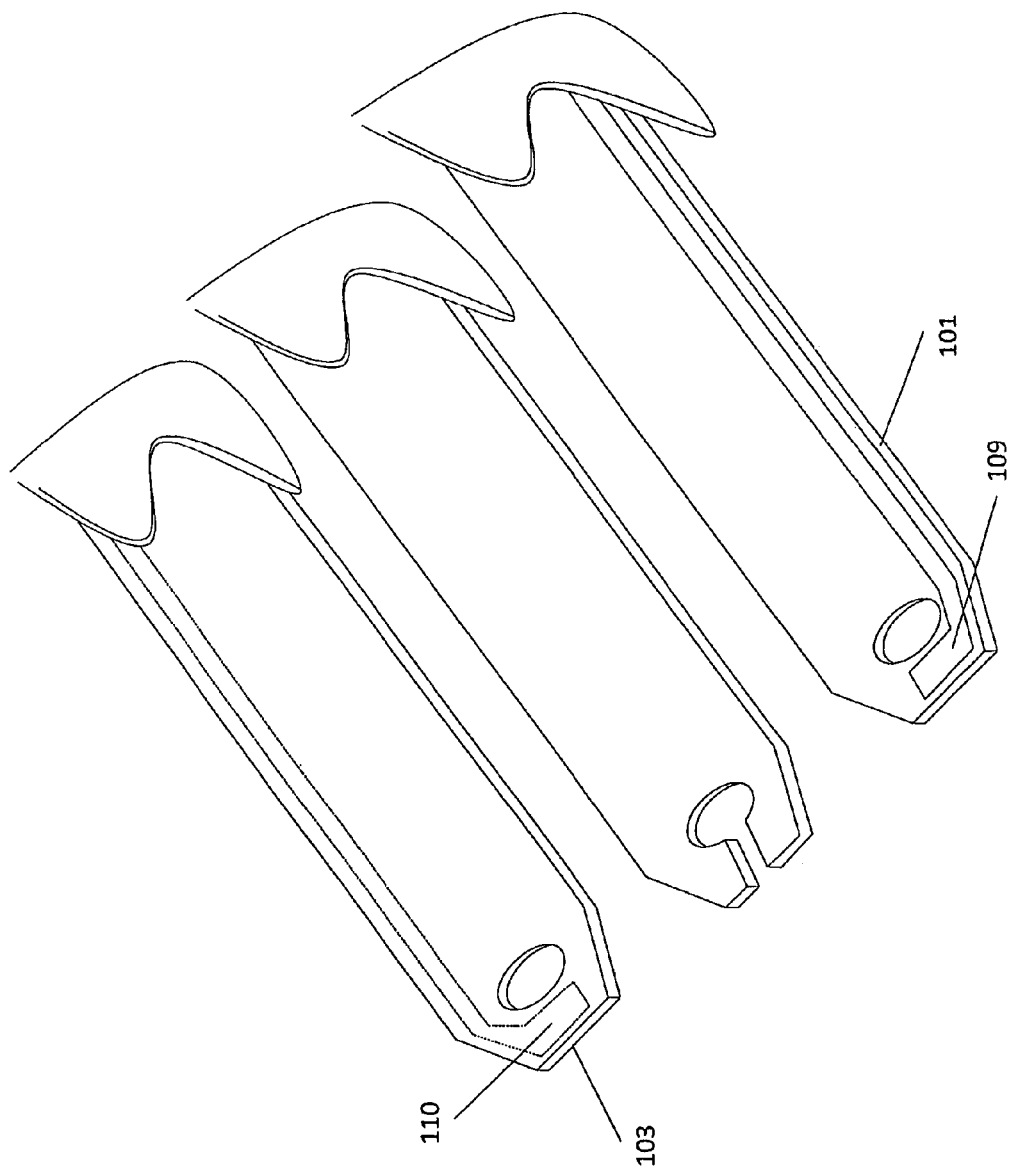

It is apparent that other embodiments known in the art can be used to construct electrochemical cells, including the use of more than two electrodes, such as three, or four, or more. In another example embodiment, FIG. 1C shows a strip which has a patterned conductive layer 109 on the bottom substrate layer 101 facing up towards the assay space and another patterned conductive layer 110 on the top substrate layer 103 facing down towards the assay space. Furthermore, as is well known in the art, the electrodes do not have to be constructed on different layers of the test strip. FIG. 1D shows another example embodiment where the electrode system is constructed on one of the substrate layers (in this example on the bottom substrate layer 101). Here, two patterned conductive layers 111 and 112 are located on the upward facing side of the bottom substrate layer 101. They can be oriented in many different positions as is commonly found in the art.

Figure 1E:
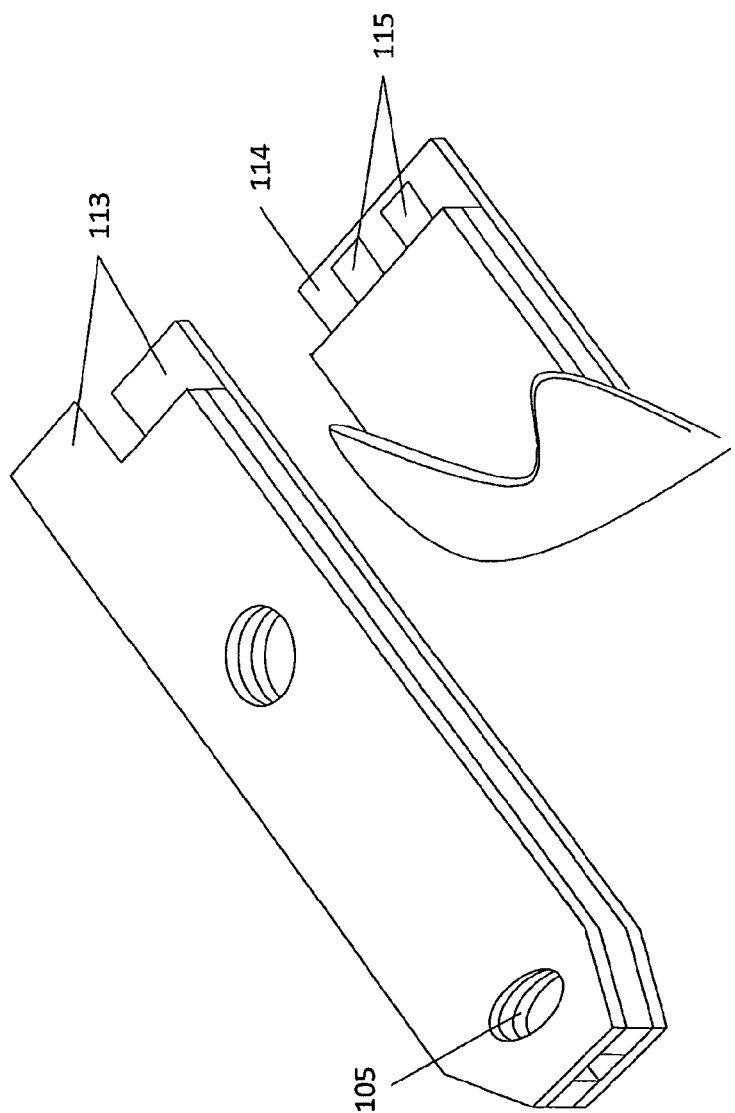

When the sample enters the assay space, air is displaced; the air can escape through the materials of the test strip if the materials are such that they allow it (for example, one of the layers 101, 102, or 103 may be constructed of a mesh material which allows air to escape. One commonly used embodiment to facilitate displacement of air as the sample enters the assay space is a dedicated opening which serves as a vent. Such a vent 105 is shown in FIGS. 1A and 1E as an opening through the entire strip. It is apparent that such a vent structure may also channel out just one of the surfaces of the strip (for example, through the top 103 or through the bottom 101). Alternatively, it can channel out a side or the rear of the strip.

The electrochemical test strip also has contact areas that are attachable to a meter to Provide an electrical connection between the meter and the portion of the test strip that are exposed in the assay space for receiving a sample and performing the assay. Such contacts are known in the art, and FIG. 1E shows some example embodiments. In the case where the inner-facing surfaces of the test strip substrate layers are covered with a conductive layer, having tabs 113 extend out from the main body of the test strip allows the strip to make electrical contact with the meter's SPC. In the example embodiment where there are patterned conductive layers on a surface, then having an extended tab 114 allows the patterned layers to extend beyond the main body of the test strip and allow the meter's SPC to make electrical contact with a portion of the conductive layer 115.

A way of manufacturing the test strips is by punching out the layers separately from large sheets of the separate layer materials, combining them, and then punching the deflectors. Alternatively, the deflector is optionally created in a layer separately before combining with the other layers, or a layer can remain unaltered with no deflector, as shown in FIG. 6. A reflective layer 1010 can be added to enhance the operation of a deflector in the case of a hole all the way through the strip layers (as shown in FIG. 4), or the reflective layer can be between a middle and an outer layer. Alternatively, the top or bottom layer can be comprised of reflective material, or additional reflective material can be used.

Top layer and bottom layer refer to the outer layers of the planar test strip. The terms "top" and "bottom" are used merely as labels and do not imply any particular orientation relative to gravity.

In one example embodiment, as shown in FIG. 6, the middle layer 102 is an electrically resistive material which isolates the conductive layers, and prevents electrical conductivity between the electrically conductive top 103 and bottom layers 101, unless they are connected via a sample disposed in the space for receiving a sample. It will be appreciated that and entire layer need not be conductive, but that at least a portion of the surface facing towards the electrochemical test space area is conductive to allow connection between the meter apparatus and the electrodes disposed in the electrochemical test space (as shown in FIG. 1C). Furthermore, both the top and the bottom layers need not comprise conductive portions; as shown in the example embodiment in FIG. 1D, one surface can comprise more than one conductive portion to make connection to electrodes disposed in the assay space.

Some examples of suitable materials for use as a middle layer include polyimide, polyester, polyethylene terephthalate (PET), polycarbonate, glass, fiberglass or other nonconductive materials that provide the desired support.

The middle layer suitably has a thickness of about 20 to 500 micrometers. Thicker materials can be used where larger sample volumes are acceptable. Thinner materials can be used, but can create difficulties in handling, and increased difficulty in drawing sample into the finished cell since this thickness determines one dimension of the assay space. In a preferred embodiment of the present invention, the assay space volume is less than 5 microliters and more preferably less than 1 microliter. In specific embodiments of the invention, the volume of the assay space is no more than 500, 300, 200, 100, 50, 20, or 10 nL.

Figure 2D:
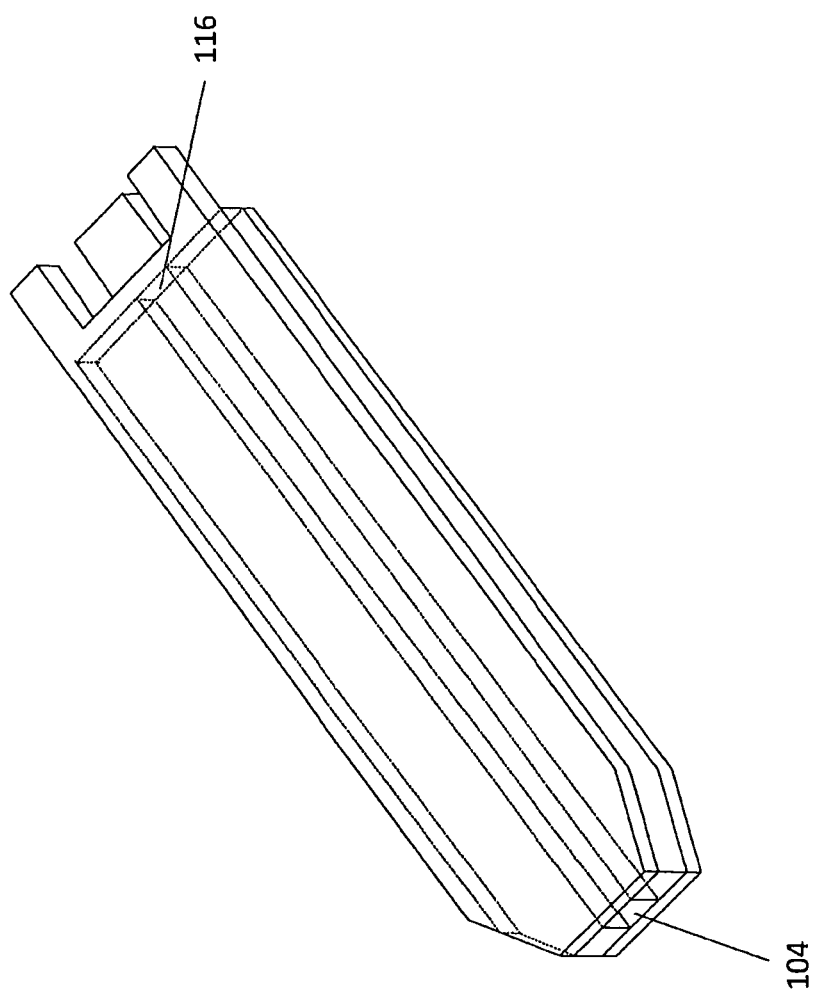

A venting chamber 121, 105 is utilized to facilitate capillary action as shown in FIGS. 2A and 6. This is an opening connected to the assay space 104 creating an air space on the opposite side from where the sample fluid contact would enter. In this example embodiment, this chamber is a hole created through the thickness of the test strip or it can be a channel space in the middle layer extending through the length of test strip, leaving an opening at both ends of the strip (the sample entry opening into the assay space 104 and the air escape vent 116), as shown in the example embodiment of FIG. 2D.

Depending on the analyte to be detected, the electrochemical test cell comprises a reagent composition disposed within the space for receiving a sample. In the case of an electrochemical cell for the detection of glucose, this reagent composition suitably comprises an enzyme effective to oxidize glucose and a redox mediator. Reagent compositions for this purpose are known in the art, for example in U.S. Pat. Nos. 4,711,245 and 5,437,999, which are incorporated herein by reference.

In addition to its electrochemical function, the reagent composition, when present, can assist in overcoming the hydrophobicity of the assay space, so that blood or other aqueous sample is drawn into the space by the hydrophilicity of the reagent. Where a reagent is not used, surface treatment of the sample volume to reduce hydrophobicity and to facilitate sample introduction is indicated, for example with Triton or other surfactants.

Notched Electrical Connectors:

In an example embodiment, the back end of the strip (i.e. the SPC tab end) is initially produced from a tabbed "parent" configuration. (FIG. 9A), and then processed by notching post-production to create varied test strip connectors. One such method of manufacturing these tabs is disclosed in U.S. patent application Ser. No. 10/908,656 filed on May 20, 2005 and published as US Pub. 2005/0258035 on Nov. 24, 2005, which is incorporated herein by reference for all purposes.

To create a parent configuration, for example, during manufacturing the top layer is created with a small tab and the bottom layer is created with a large tab where the small tab is relatively smaller than the large tab. For example, as shown in FIGS. 9A-B, the small tab is approximately one quarter the total width of the entire strip. In addition, as shown in FIGS. 9A-B, the small tab is situated all the way to one side of the strip, while the large tab is situated all the way to the other side.

From this parent configuration, two child configurations can be made by removing (for example by notching or punching or laser cutting) sections of the parent tabs. (FIGS. 10A-B, 11A-B). FIGS. 10A-B show the notching done at the side of the large tab closest to the small tab. FIGS. 11A-B show the notching done in the middle of the large tab.

In the FIGS. 9A, 9B, 10A, 10B, 11A, 11B, 14A, and 14B, the interior face (the face that is closest to the middle layer 932) of both the top and bottom layer is electrically conductive material that is connected to the electrochemical cell. This provides the connection from the electrochemical cell to the strip port connector and into the analyte meter. After assembly of the strip and optionally after QC and calibration activities are finished, the top sheet 935 and the bottom sheet 930 of "parent configuration" strips can be altered into the final commercial configuration.

Figure 14B:
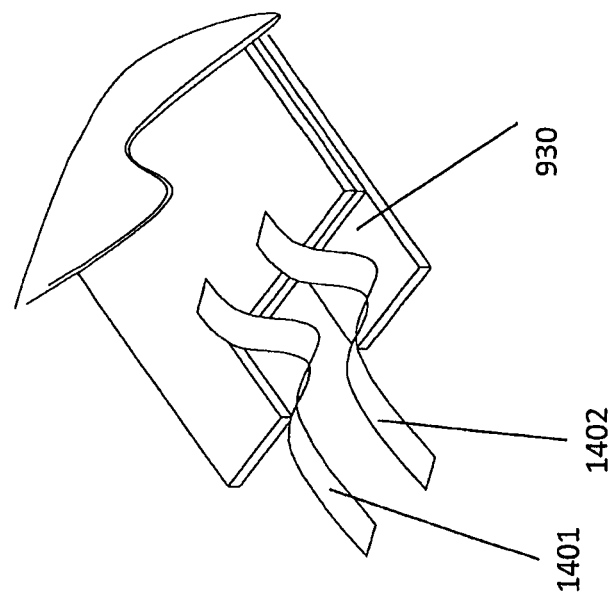
FIGS. 14 A-I show several configurations of contact made between the strip port connector contact pins and the conductive surface of the strip.
Figure 14A:
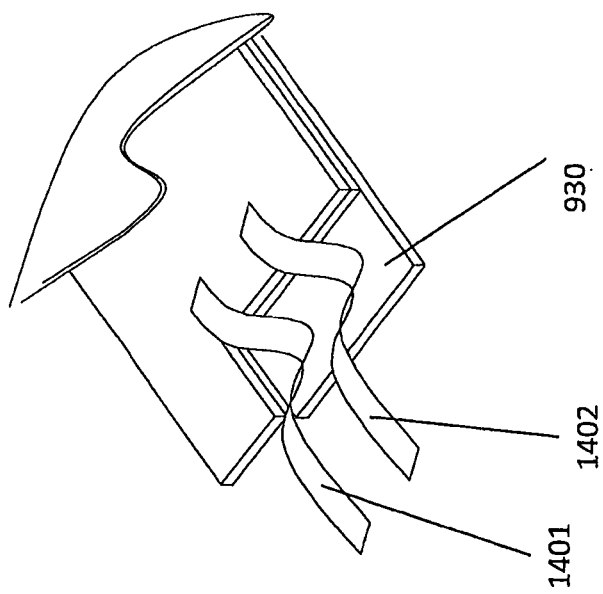

FIGS. 14A and B illustrate an example showing how the SPC contact pins 1401 and 1402 can both make contact with the conductive surface 930 in the case where the parent configuration is used. In this case, the meter apparatus can detect electrical conductivity between the pins 1401 and 1402 and identify the strip as having characteristics associated with the parent configuration. In the example of FIG. 14B, once child configuration is created by removing that portion of conductive surface 930 such that SPC pin 1401 does not make electrical contact with the strip. In this case, the meter apparatus can detect that there is no electrical conductivity between pins 1401 and 1402 and identify the strip as having characteristics associated with a child configuration.

Figure 14C:
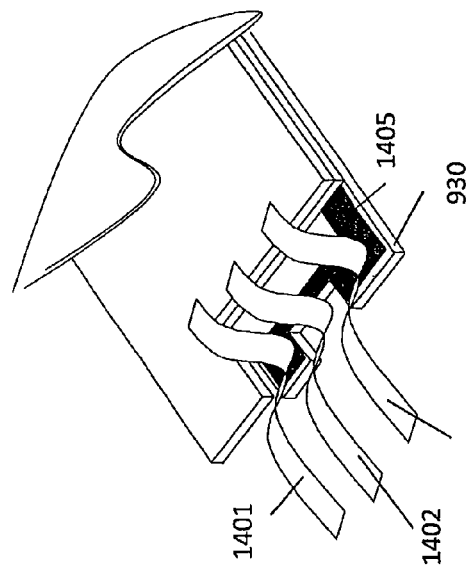
Figure 14D:
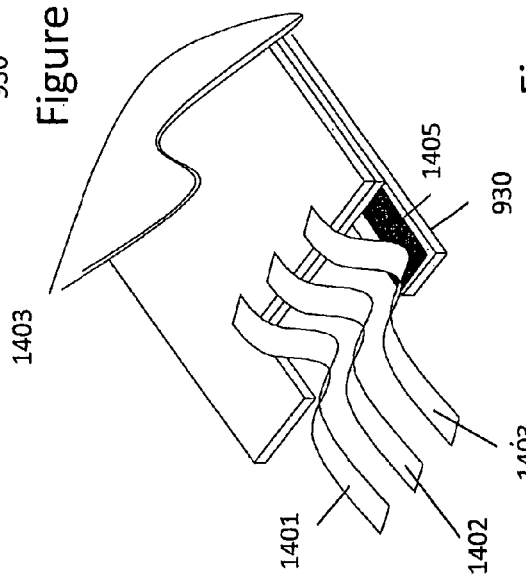

Other example constructions are also possible, as shown in FIGS. 14C-14I. In these embodiments, the entire surface of the bottom layer is not conductive, but rather a patterned portion of the surface is conductive. In FIG. 14C, a parent configuration is shown where the bottom layer 930 has a patterned conductive portion 1405 which makes contact with all three SPC pins 1401, 1402, 1403. In this example, the conductive portion 1405 also connects the SPC pins to an electrode disposed in the assay space. FIGS. 14D, E, F illustrate example embodiments where portions of the bottom layer 930 have been removed to allow for different child configurations. It will be appreciated that these are not exhaustive embodiments and are only illustrative examples. In FIG. 14D, a portion of the bottom layer 930 has been removed such that only pins 1401 and 1403 are in electrical contact with each other via conductive portion 1405. In this case, the meter apparatus can detect that there is no electrical conductivity between pins 1401 and 1402, no electrical conductivity between pins 1402 and 1403, but that there is electrical conductivity between pins 1401 and 1403, and identify the strip as having characteristics associated with this child configuration. It will also be appreciated that the removal of a portion of conductive portion 1405 may be accomplished by means other than removal of the entire thickness of layer 930; for example, methods such as laser ablation, kiss cutting, or scratching of the surface may be used to remove portions of 1405 to electrically isolate the portion of the strip that contacts pin 1402 from the portions of the strip that make electrical contact with pins 1401 and 1402. Furthermore, the meter apparatus may also be configured to measure the amount of conductivity between pins 1401 and 1403 to make a determination of the configuration. It is known in the art that the resistance of a conductor changes with its cross-sectional geometry. Thus, if the remaining segment of 1405 that connects pins 1401 and 1403 is thin, the resistance between them is higher than if that segment is thicker. Using this method, more child configurations may be obtained if different amounts of 1405 are removed.

Figure 14E:
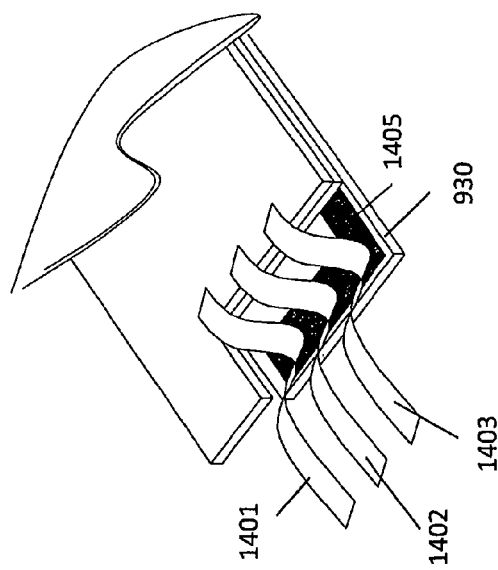

In FIG. 14E, a different portion of layer 930 is removed, thereby causing electrical contact between pins 1402 and 1403 only and leaving pin 1401 electrically isolated from the other two pins. The meter apparatus can detect the combination of pins which are in electrical contact with each other and recognize this child configuration.

Figure 14F:
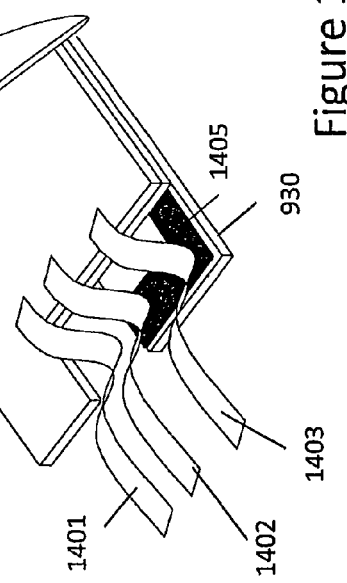

In FIG. 14F, a different portion of layer 930 is removed, thereby causing electrical contact to be broken between all three pins. The meter apparatus can be programmed to detect that no pins are in electrical contact with each other and recognize this child configuration.

FIG. 14G shows an example embodiment of a parent configuration with two conductive portions 1405 and 1406 disposed on the bottom layer 930. SPC pins 1401 and 1402 are in electrical contact with each other via conductive portion 1406; SPC pins 1403 and 1404 are in electrical contact with each other via conductive portion 1405. The meter apparatus can detect this state and recognize it as the parent configuration. In FIG. 14H, a portion of bottom layer 930 is removed such that none of the pins are in electrical contact with each other. The meter apparatus can detect this state and recognize it as one child configuration. In FIG. 14I, a portion of bottom layer 930 is removed such that only pins 1403 and 1404 are in electrical contact with each other via 1405. The meter apparatus can detect this state and recognize it as another child configuration.

The SPC should be configured such that it detects the varied patterns of connectivity, for example with a multiplicity of electrical connectors. Alternatively, the strip port connector can be configured with connectors only at locations that will come into contact with a properly notched test strip end. In addition, the test strips can combine notched ends with punched deflectors to provide even more possible configurations.

The examples provided above merely provide embodiments of possible methods of creating notched electrical connectors. There are numerous possible variants to the configurations provided. It should also be appreciated that a notched electrical connector can be used with a test strip utilizing the above described deflectors, or separately, on a test strip with no deflectors. This notching pattern can be used in combination with deflectors, or independently.

Apparatus and Analyte Test Meter:

The analyte meter of the present invention comprises a light source, a photodetector, and a SPC.

The light used is generated from within the analyte testing meter or other apparatus at a photogenerator 1080, such as shown in FIGS. 3A, B. The light is generated from, for example, a light-emitting diode (LED), fluorescence, phosphorescence, incandescence, halogen, chemoluminescence or electroluminescence.

The light is directed into the optical waveguide, for example through the strip port connector, where the strip interfaces with the meter. Alternatively, the light source is part of the strip port connector, or the light can be directed to enter the waveguide of the strip from a point outside of the SPC.

As shown in FIGS. 3A, B, the light 5101, 5102, 5103 can travel through the test strip and out the other end 1050. If there are any deflectors 131 in the test strip, a portion of the light will exit the strip 1090, and a portion of it will continue moving through the waveguide(s) to exit the end of the strip 1050.

Experience with users permits selecting an LED color that is well suited to the task. For example a blue or yellow-green LED will offer very good contrast when the user is trying to find a drop of red blood, working better than a red LED. This light can also be turned on before the strip is inserted, aiding the user in inserting the test strip.

The meter of the present invention also comprises a photodetector, used to determine when light has escaped from a deflector. A variety of photodetectors are known in the art and some are described above.

The photodetector of the meter can be a single detector, to detect any light transmitted, or it can be an array of photodetectors, whether in a line, a grid, or a geometric arrangement, that can detect a pattern of deflectors.

These photodetectors can be sensitive to any light, or can be configured to determine the level/amount/intensity of light transmitted.

A photodetector 100 can be positioned so that it views only one side of the test strip while the strip is inserted, as illustrated in FIGS. 3A, B, or there can be photodetectors 100 located to view the top and the bottom of the strip, as illustrated in FIG. 8.

The SPC is used to interface with a test strip using electrical connections that can establish electrical contact with electrodes located on the test strip.

The SPC can incorporate a photogenerator to direct light into the optical waveguide, or it has a hole or a slot so that light generated behind it passes through it and into the optical waveguide, or it can be made of optically-transmissive material (for example clear plastic) so that light generated on one side of it can pass through to the test strip waveguide.

This SPC can have a multiplicity of electrical connectors (for example, metal pins) to accommodate test strips with varying connector locations, such as strips with notching patterns as shown in FIGS. 9A-11B, and 14A-I. This SPC can be used with test strips from a variety of manufacturers, or it can interface with test strips from a single manufacturer that uses various configurations to encode characteristics about the test strips.

As shown in FIG. 8, a test strip receiving area 128 is the portion of an analyte testing meter that guides a test strip 800 to the strip port connector 120 (for the sake of clarity, the pins of the SPC 120 have not been drawn). It has an open insertion point at one end, and the strip port connector 120 is at the other end. The receiving area 128 should be shaped to guide the test strip 800 to be inserted in the proper configuration. Reflective material can placed along the walls of the receiving area 128 to reflect and focus light 102 emitted from the test strip 800. In addition, photodetectors 100 can be placed along the walls to detect light 1090 emitted from the test strip 800 at deflector 831.

In some embodiments, the use of variously tabbed and notched strips can change the amount of light striking the detectors. For example, if there is more light entering one layer, perhaps due to the bottom 930 tab being wider, as in the configuration shown in FIG. 9A, then more light may hit a photodetector situated in the meter apparatus to face the bottom layer 930 even in the absence of an deflector. This would result in a different baseline signal in the off (or "no deflector") configuration. If the meter is able to determine the orientation of the strip inserted, then this baseline signal (for the off/no deflector configuration) and the on/with deflector configuration is be compared to the correct threshold levels. The meter can thus be pre-calibrated to know how much light is expected to leak from each of the notch configurations. Alternatively, the meter apparatus can measure the amount of light leaking through the test strip material, for example through an extra photo detector situated at a location away from a deflector position.

The invention claimed is:

1. A method for determining a characteristic of an electrochemical test strip comprising
   (A) providing a test strip having an electrical connector at a first end, an electrochemical test cell at a second opposite end, a waveguide extending from the first end towards the second end, and a deflector formed in or on the waveguide, said deflector suitable for deflecting at least a portion of light traveling along the waveguide so that the deflected light exits the waveguide between the first end and second end of the strip;
   (B) inserting the first end of the strip into an apparatus, said apparatus comprising a light source and a photodetector, said light source being disposed to introduce light into the first end of the waveguide and said photodetector being disposed to detect the deflected light exiting the waveguide;
   (C) directing light into the waveguide;
   (D) detecting the deflected light exiting the waveguide; and
   (E) correlating the detected light with a characteristic.

2. The method of claim 1 wherein the waveguide extends to the second end of the strip and wherein light exits the waveguide at the second end of the strip.

3. The method of claim 1 wherein the characteristic is regional identification.

4. The method of claim 1 wherein the characteristic is calibration information.

5. The method of claim 1 wherein the characteristic is the type of analyte measured by the test strip.

6. The method of claim 1 wherein the characteristic is alignment of the test strip with the apparatus.

7. The method of claim 1 wherein a plurality of deflectors are formed in or on the waveguide and the photodetector detects light deflected by the plurality of deflectors as separate signals.

8. The method of claim 1 wherein the apparatus comprises an analyte test meter having a strip port connector for interaction with the electrical connector of the test strip and having electronics to determine an amount of an analyte in a sample applied to the electrochemical test cell of the test strip and wherein the photodetector and the photogenerator are contained in the analyte test meter.

9. The method of claim 1 wherein said test strip further comprises a top substrate and a bottom substrate; wherein the waveguide is sandwiched between the two substrates.

10. The method of claim 1 wherein said test strip further comprises
    a top substrate;
    a bottom substrate;
    wherein said electrical connector electrically connects the electrochemical test cell with a strip port connector of a meter and comprises a first tab formed at the first end of the top substrate layer, and a second tab formed at the first end of the bottom substrate layer;
    wherein the first tab is small in width relative to the second tab; and
    wherein the first tab is not aligned with the second tab.

11. An elongated test strip comprising
    an electrical connector at a first end,
    an electrochemical test cell at a second opposite end,
    a waveguide extending from the first end towards the second end, and a deflector formed in or on the waveguide, wherein said deflector is suitable for deflecting at least a portion of light traveling along the waveguide so that the deflected light exits the waveguide between the first end and second end of the strip.

12. The test strip of claim 11 wherein one or more additional deflectors are formed in or on the waveguide.

13. A combination of the test strip of claim 11 and an analyte test meter wherein the analyte test meter detects light exiting the deflector formed in or on the waveguide and correlates detected light with a characteristic of the strip.

14. The combination of claim 13 wherein the characteristic is regional identification.

15. The combination of claim 13 wherein the characteristic is calibration information.

16. The combination of claim 13 wherein the characteristic is the type of analyte measured by the test strip.

17. The combination of claim 13 wherein the characteristic is alignment of the test strip with the analyte test meter.

18. An elongated test strip comprising
    (a) a first deflector surface and a second deflector surface;
    (b) an optical waveguide disposed between the first and second deflector surfaces extending from a first end towards a second end of the test strip, whereby light cast into the waveguide at the first end is emitted from the waveguide at the second end;
    (b) an strip port connector disposed at the first end; and
    (c) an electrochemical test cell disposed at the second end;
    wherein a first deflector is formed in the optical waveguide, a second deflector is formed in the first deflector surface and a second deflector is formed in the second deflector surface;
    wherein the first, second, and third deflectors are aligned;
    wherein said deflectors are not contiguous with the electrochemical cell; and
    further comprising a reflective material placed over the second deflector such that light is directed back through the first, second, and third deflectors.

19. The test strip of claim 18 wherein one or more additional deflectors are formed in the waveguide and/or the first deflector surface and/or bottom surface; and wherein said deflectors are not contiguous with the electrochemical cell.

20. The test strip of claim 18 having at least one characteristic and an deflector pattern corresponding to said characteristic.

21. The test strip of claim 20 wherein the characteristic is regional identification.

22. The test strip of claim 20 wherein the characteristic is calibration information.

23. The test strip of claim 20 wherein the characteristic is the type of analyte measured by the test strip.

24. The test strip of claim 18 wherein the deflector indicates alignment of the test strip.

25. An elongated test strip comprising
    (a) a top surface;
    (b) a bottom surface;
    (c) an optical waveguide disposed between the top and bottom surfaces and extending from a first end towards a second end of the test strip, whereby light cast into the waveguide at the first end is emitted from the waveguide at the second end;
    (d) an electrical connector for connection to a meter disposed at the first end; and
    (e) an electrochemical test cell disposed at the second end;
    wherein a first deflector and a second deflector are formed in the optical waveguide, a third deflector is formed in the top surface and a fourth deflector is formed in the bottom surface;
    wherein the third and fourth deflectors are not aligned;
    wherein the first and third deflectors are aligned and the second and fourth deflectors are aligned; and
    wherein said deflectors are not contiguous with the electrochemical cell.

26. The test strip of claim 25 wherein said first and second deflectors are aligned.

27. The test strip of claim 25 having a first plurality of deflectors on the top surface and a second plurality of deflectors on the bottom surface; and wherein said deflectors are not contiguous with the electrochemical cell.

28. The test strip of claim 25 having at least one characteristic and a deflector pattern corresponding to said characteristic.

29. The test strip of claim 28 wherein the characteristic is that the test strip is not counterfeit.

30. The test strip of claim 28 wherein the characteristic is regional identification.

31. The test strip of claim 28 wherein the characteristic is calibration information.

32. The test strip of claim 28 wherein the characteristic is the type of analyte measured by the test strip.

33. The test strip of claim 25 wherein the deflector indicates alignment of the test strip.

34. A combination of a test strip and a test meter, wherein
    (a) said test strip comprises
        an electrical connector at a first end,
        an electrochemical test cell at a second opposite end,
        a waveguide extending from the first end towards the second end, and
        a deflector formed in or on the waveguide, wherein said deflector is suitable for deflecting at least a portion of light traveling along the waveguide so that the deflected light exits the waveguide between the first end and second end of the strip,
    (b) said test meter comprises
        a strip port connector for interaction with the electrical connector of the test strip,
        electronics to determine an amount of an analyte in a sample applied to the electrochemical test cell of the test strip, and
        a photogenerator for generating and directing light into the first end of the waveguide are contained in the analyte test meter,
        a photodetector for detecting deflected light exiting the waveguide,
    wherein the first end of the test strip is disposed in the strip port connector of the test meter.

35. The test strip of claim 34 wherein one or more additional deflectors are formed in or on the waveguide, wherein said deflectors are not contiguous with the electrochemical cell.

36. A test strip comprising
    (a) a top substrate extending the full length of the strip;
    (b) a bottom substrate extending the full length of the strip;
    (c) an electrical connector for connection to a meter disposed at a first end; and
    (d) an electrochemical test cell disposed at a second end;
        wherein said electrical connector comprises a first tab formed at the first end of the top substrate, and a second tab formed at the first end of the bottom substrate;

wherein the first tab is small in width relative to the second tab;

wherein the first tab is not aligned with the second tab;

wherein the test strip further comprises an optical waveguide disposed between the top and bottom surfaces and extending from the first end towards the second end of the test strip, whereby light cast into the waveguide at the first end is emitted from the waveguide at the second end; and wherein a first deflector is formed in the optical waveguide such that light exiting the waveguide via the deflector is visible through a surface of the strip.

37. The test strip of claim 36 wherein the second tab is notched in the middle of the tab.

38. The test strip of claim 36 wherein the second tab is notched on the edge closest to the first tab.

39. The test strip of claim 36 wherein the second tab is notched on the edge farthest from the first tab.

40. A set of test strips of claim 36 further comprising a plurality of subgroups wherein all test strips in the same subgroup detect the same analyte and are prepared in a single manufacturing process and wherein notches are formed in the second tab of all or all but one of the subgroups to distinguish between subgroups.

41. A test strip comprising
(a) a top surface;
(b) a bottom surface;
(c) two edges;
(d) an optical waveguide disposed between the top and bottom surfaces and extending from a first end towards a second end of the test strip, whereby light cast into the waveguide at the first end is emitted from the waveguide at the second end;
(e) an electrical connector for connection to a meter disposed at the first end; and
(f) an electrochemical test cell disposed at the second end;
(g) an deflector punched through the optical waveguide such that light exiting the optical waveguide exits through an edge of the test strip.

42. An electrochemical test strip comprising:
an electrical connector with a plurality of electrical contact areas disposed at a first end;
an electrochemical test cell;
a waveguide extending from the first end toward second end of the strip; and
a plurality of apertures formed through the waveguide between the first and second ends, wherein said apertures deflect a portion of light traveling along the waveguide so that the deflected light exits the test strip through the apertures, and wherein at least one aperture is of different size than another aperture.

43. The test strip of claim 42, wherein the waveguide extends to the second end of the strip and wherein light exits the waveguide at the second end of the strip.

44. A method for determining a characteristic of an electrochemical test strip, the method comprising:
(A) providing a test strip comprising: an electrical connector with a plurality of electrical contact areas disposed at a first end; an electrochemical test cell; a waveguide extending from the first end towards a second end of the strip; and a plurality of apertures formed through the waveguide between the first and second ends, wherein said apertures deflect a portion of light traveling along the waveguide so that the deflected light exits the test strip through the apertures, and wherein at least one aperture is of different size than another aperture;
(B) directing light into the waveguide and detecting the location and intensity of the deflected light exiting the test strip through the apertures; and
(C) determining a characteristic of the electrochemical test strip, from the deflected light detected in step (B).

45. The method of claim 44, further comprising the step of:
(D) making electrical contact with the plurality of contact areas of the test strip,
wherein the characteristic of step (C) is further determined from the electrical contacts made in step (D).

46. The method of claim 44, wherein the waveguide extends to the second end of the strip and wherein light exits the waveguide at the second end of the strip.

47. The method of claim 44, wherein the characteristic is regional identification, calibration information, counterfeit information, analyte information, test strip alignment information, brand information, manufacturer information, or any combination thereof.

* * * * *